US006982252B2

(12) United States Patent
Paglin et al.

(10) Patent No.: US 6,982,252 B2
(45) Date of Patent: Jan. 3, 2006

(54) INHIBITION OF VACUOLAR PROTON ATPASE ACTIVITY AND/OR THE MODULATION OF ACIDIC ORGANELLE FUNCTION SENSITIZES CELLS TO RADIATION, CHEMOTHERAPY AND BIOLOGICAL AGENTS

(75) Inventors: Shoshana Paglin, New York, NY (US); Joachim Yahalom, New York, NY (US); Timothy Hollister, Chicago, IL (US); Thomas Delohery, Oakland, NJ (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 216 days.

(21) Appl. No.: 10/006,957

(22) Filed: Dec. 4, 2001

(65) Prior Publication Data

US 2002/0156025 A1 Oct. 24, 2002

Related U.S. Application Data

(60) Provisional application No. 60/251,153, filed on Dec. 4, 2000.

(51) Int. Cl.
*A01N 43/04* (2006.01)
*A01N 43/02* (2006.01)
*A61K 31/70* (2006.01)
*A61K 31/335* (2006.01)

(52) U.S. Cl. .......................... 514/28; 514/450; 424/9.2; 424/138.1

(58) Field of Classification Search .................. 514/28, 514/450; 424/9.2, 138.1

See application file for complete search history.

(56) References Cited

FOREIGN PATENT DOCUMENTS

WO    WO 90/11364    10/1990

OTHER PUBLICATIONS

Okahashi et al., "Specific Inhibitors of Vacuolar H+ − ATPase Trigger Apoptotic Cell Death of Osteoclasts", Journal of Bone and Mineral Research, vol. 12, No. 7, 1997.*
Drose et al., "Review—Bafilomycins and Concanamycins as Inhibitors of V−ATPases and P−ATPases", The Journal of Experimental Biology, 200, pp. 1–8, 1997.*
Altan et al., "Defective Acidfication in Human Breast Tumor Cells and Implications for Chemotherapy", J. Exp. Med., vol. 187:10, pp. 1583–1598 (1998).*
Boyd et al., "Discovery of Novel Antitumor Benzolacetone Enamide Class That Selectively Inhibits Mammalian Vacuolor–Type (H+)–ATPases", Journal of Pharmacology and Experimental Therapeutics, 297, pp. 114–120 (2001).*

Altan et al., Defective Acidfication in Human Breast Tumor Cells and implications for Chemotherapy, J. Exp. Med., vol. 187:10, pp. 1583–1598 (1998) Bechimol et al., Functional Expression of Vacuolar–type H+–ATPase in the plasma membrane and intr.*
Bechimol et al.,Functional Expression of a Vacuolar–type H+–ATPase in the plasma membrane and intracellular vacuoles of Trypanosoma cruzi, Biochem.J., V:332, p. 695–702 (1998).*
Teicher et al. Signal Transduction Inhibitors As Modifiers Of Radiation Therapy In Human Prostate Carcinoma Xenografts, Radiation Oncology Investigations, 4/5, pp. 221–230 (1986).*
Furuya et al., The Role Of Calcium, Ph, And Cell Proliferation in The Programmed (Apoptotic) Death Of Androgen–Independent Prostatic Cancer Cells Induced By Thapsigargin, Cancer Res., 54/23, pp. 6167–6175 (1994).*
Boyd MR et al., 2001, "Discovery of a novel antitumor benzolactone enamide class that selectively inhibits mammalian vacuolar–type (H+)–atpases" *J. Pharmacology and Experimental Therapeutics* 297(1):114–120.
Gingras AC et al., 2001, "Regulation of translation initiation by FRAP/mTOR" *Genes and Development* 15:807–826.

(Continued)

*Primary Examiner*—James O. Wilson
*Assistant Examiner*—Traviss C. McIntosh, III
(74) *Attorney, Agent, or Firm*—Edwards & Angell, LLP; Amy M. Leahy

(57) ABSTRACT

The present invention relates to methods and compositions for inhibiting cell survival and/or promoting cell death following exposure to cytotoxic agents and stress such as radiation or chemotherapy exposure through inhibition of V-H$^+$-ATPase. In particular, the formation and/or acidification of acidic vesicular organelles (AVOs) may be prevented or decreased by inhibiting the activity of vacuolar proton ATPase ("V-H$^+$-ATPase"). The methods and compositions of the invention are based on the observation that (i) following irradiation surviving cancer cells accumulate AVOs and that their acidification is mediated by V-H$^+$-ATPase; (ii) surviving colonies of cells contain higher levels of AVOs; and (iii) inhibition of V-H$^+$-ATPase decreases the clonogenic survival of cells irradiated or exposed to chemotherapeutic agents. These observations led to the conclusion that V-H$^+$-ATPase activity and AVO function serve to protect cells from radiation and chemotherapy damage. In addition, agents such as bFGF, TNF-α, PMA, rapamycin and tamoxifen were shown to be inducers of acidic organelle formation. Therefore signal transduction pathways mediated by these agents provide targets for drug screening assays designed to identify inhibitors of V-H$^+$-ATPase activity and AVO formation/acidification. The present invention may be used to treat cancer subjects through sensitization of neoplastic cells to the toxic effects of radiation and chemotherapy.

22 Claims, 12 Drawing Sheets

OTHER PUBLICATIONS

Figure 1A:
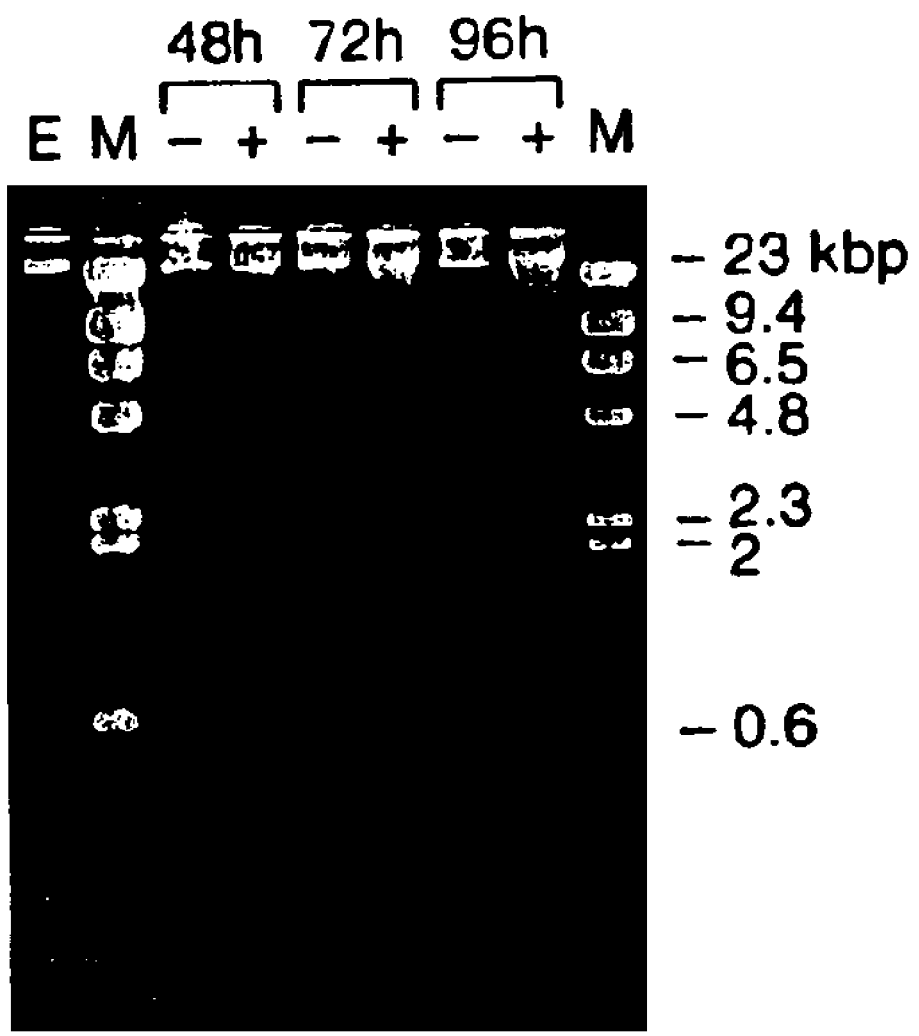

Murakami T et al., 2001, "Elevated expression of vacuolar proton pump gene and cellular pH in cisplatin resistance" *Int. J. Cancer 93:*869–874.

Paglin S et al., 2001, "A novel response of cancer cells to radiation involves autophagy an formation of acidic vesicles" *Cancer Res. 61:*439–444.

Hollister TC et al., Nov. 4–8, 2001, "Vacuolar–proton–ATPase is involved in the response of cancer cells to ionizing radiation and is a new target for radiosensitization", *43rd Annual American Society for Therapeutic Radiology and Oncology* (ASTRO).

Xu T et al., 2001, "Microtubules are involved in glucose–dependent dissociation of the yeast vacuolar [H+]-ATPase in vivo", *J Biol Chem. 276*(27):24855–24861.

Gilles F et al., 2000, "A. MUC1 dysregulation as the consequence of a t(1;14)(q21;q32) translocation in an extranodal lymphoma" *Blood 95*(9):2930–2936.

Kim J et al., 2000, "Autophagy, cytoplasm-to-vacuole targeting pathway, and pexophagy in yeast and mammalian cells", *Ann. Rev. Biochem. 69:*303–342.

Petiot A et al., 2000, "Distinct classes of phosphatidylinositol 3'-kinases are involved in signaling pathways that control macroautophagy in HT–29 cells" *J. Biol. Chem. 275*(2):992–998.

Finkel E, 1999, "Does Cancer therapy trigger cell suicide?" *Science 286*(5448):2256–2258.

Reed J, 1999, "Dysregulation of apoptosis in cancer" *J Clin Oncol. 17*(9):2941–2953.

Forgac M, 1999, "Structure and properties of the vacuolar (H+) ATPases" *J. Biol. Chem. 274*(19):12951–12954.

Brown JM et al., 1999, "Apoptosis, p53, and tumor cell sensitivity to anticancer agents" *Cancer Research 59:*1391–1399.

Thangara M et al., 1999, "Interdependent regulation of intracellular acidification and SHP–1 in apoptosis" *Cancer Research 59:*1649–1654.

Gagliardi S et al., 1999, "Chemistry and structure activity relationships of bafilomycin A1, a potent and selective inhibitor of the vacuolar H+–ATPase" *Current Medicinal Chemistry 6*(12):1197–1212.

Mizushima N et al., 1998, "A new protein conjugation system in human. The counterpart of the yeast Apg12p conjugation system essential for autophagy" *J Biol Chem. 273*(51):33889–33892.

Mizushima N et al., 1998, "A protein conjugation system essential for autophagy" *Nature 395*(6700):395–398.

Altan N et al., 1998, "Defective acidification in human breast tumor cells and implications for chemotherapy" *J Exp Med. 187*(10):1583–1598.

Jänicke RU et al., 1998, "Caspase–3 is required for DNA fragmentation and morphological changes associated with apoptosis" *J. Biol. Chem. 273*(16):9357–9360.

Noda T et al., 1998, "Tor, a Phosphatidylinositol Kinase Homologue, Controls Autophagy in Yeast" *J. Biol. Chem. 273*(7):3963–3966.

Hammond EM et al., 1998, "Homology between a human apoptosis specific protein and the product of APG5, a gene involved in autophagy" *FEBS Lett. 425:*391–395.

Ohta T et al., 1998, "Bafilomycin A1, induces apoptosis in the human pancreatic cancer cell line CAPAN–1" *J. Pathology 185:*324–340.

Blommaart EFC et al., 1997, "Autophagic proteolysis: control and specificity" *Biochem. Journal 29:*365–385.

Dröse S et al., 1997, "Bafilomycin and concanamycins as inhibitors of V–ATPases and P–ATPases" *J. Exp. Biology 200:*1–8.

Jia L et al., 1997, "Inhibition of autophagy abrogates tumour necrosis factor a induced apoptosis in human T–lymphoblastic leukaemic cells" *British Journal of Haematology 98:*673–685.

Keeling DJ et al., 1997, "Vacuolar (H+)–ATPases. Targets for drug discovery?" *Ann. N.Y. Acad Sciences 834:*600–608.

Paglin S et al., 1997, "Radiation–induced micronuclei formation in human breast cancer cells: Dependence on serum and cell cycle distribution" *Biochem and Biophys Research Communications 237*(RC977117):678–684.

Bristow RG et al., 1996, "The p53 gene as a modifier of intrinsic radiosensitivity: implications for radiotherapy" *Radiotherapy and Oncology 40:*197–223.

Bursch W et al, 1996, "Active cell death induced by the anti–estrogens tamoxifen and ICI 164 384 in human mammary carcinoma cells (MCF–7) in culture: the role of autophagy" *Carcinogenesis 17:*1595–1607.

Verheij M et al., 1996, "Requirement for ceramide initiated SAPK/JNK signaling in stress–induced apoptosis" *Nature 380:*75–79.

Bose R et al., 1995, "Cermide synthase mediates Daunorubicin–induced apoptosis: An alternative mechanism for generating death signals" *Cell. 82:*405–414.

Boyd MR et al., 1995, "Some practical considerations and applications of the National Cancer Institute in vitro anticancer drug discovery screen" *Drug Dev. Res. 34:*91–109.

Gottlieb RA et al., 1995, "Cell acidification in apoptosis: granulocyte colony–stimulating factor delays programmed cell death in neurophils by up–regulating the vacuolar H(+)–ATPase" *Proc Natl Acad Sci USA 92:*5965–5968.

Lee BS et al., 1995, "Transcriptional regulation of the vacuolar H(+)–ATPase B2 subunit gene in differentiating THP–1 cells" *J. Biol. Chem. 270*(13):7320–7329.

Zakeri Z et al., 1995, "Cell death: programmed, apoptosis, necrosis, or other?" *cell Death and Differentiation 2:*87–96.

Bronstein I et al., 1994, "Chemiluminescent reporter gene assays: sensitive detection of the GUS and SEAP gene products" *Biotechniques 17*(1):172–177.

Haimovitz–Friedman A et al., 1994 "Ionizing radiation acts on cellular membranes to generate ceramide and initiate apoptosis" *J. Exp. Med. 180:*525–535.

Palokangas H et al., 1994, "Active vacuolar H+–ATPase is required for both endocytic and exocytic processes during viral infection of BHK–21 cells" *J Biol Chem. 269*(26):17577–17585.

Houghton AN et al., 1994, "A Tribute to Zanvil Alexander Cohn, (1926–1993)" *J. Exp. Med. 179:*1–30.

Traganos F et al. 1994, "Lysosomal proton pump activity; Supravital cell staining with acridine orange differentiates leukocytes subpopulations" *Methods in Cell Biology 41:*185–194.

Wollman R et al., 1994, "Effect of epidermal growth factor on the growth and radiation sensitivity of human breast cancer cells in vitro" *Int J Radiation Oncol Biol Phys. 30*(1):91–98.

Manabe T et al., 1993, "Inhibitors of vacuolar–type H(+)–ATPase suppresses proliferation of cultured cells" *J. Cell Physiol. 157:*445–452.

Schwartz LM et al., 1993, "Do all programmed cell deaths occur via apoptosis?" *Proc. Natl. Acad Sci. USA 90:*980–984.

Songyang Z et al., 1993, "SH2 domains recognize specific phosphopeptide sequences" *Cell* 72:767–778.

van Hille B et al., 1993, "Identification of two subunit A isoforms of the vacuolar H(+)–ATPase in human osteolastoma" *J. Biol. Chem.* 268(10):7075–7080.

Lenk SE et al., 1992, "Ubiquitin–activating enzyme, E1, is associated with maturation of autophagic vacuoles" *J. Cell Biology* 118(2):301–308.

Maher LJ, 1992, "DNA triple–helix formation: an approach to artificial gene repressors?" *Bioessays* 14(12):807–815.

Metzelaar JM et al., 1992, "Lysosomal membrane glycoproteins in platelets" *Thrombosis and Haemostasis* 68(4):378–382.

Gillespie GA et al., 1991, "CpG island in the region of an autosomal dominant polycystic kidney disease locus defines the 5' end of a gene encoding a putative proton channel" *Proc. Natl. Acad. Sci USA* 88:4289–4293.

Hélène C, 1991, "The anti–gene stragegy: control of gene expression by triplex–forming–oligonucleotides" *Anticancer Drug Des.* 6:569–584.

Houghton RA et al., 1991, "Generation and use of synthetic peptide combinatorial libraries for basic research and drug discovery" *Nature* 354:84–86.

Lam KS et al., 1991, "A new type of synthetic peptide library for identifying ligand–binding activity" *Nature* 354:82–84.

Roberts CJ et al., 1991, "Methods for studying the yeast vacuole" *Methods In Enzymol.* 194:644–661.

Yeh HI et al., 1991, "Proton accumulation and ATPase activity in Golgi apparatus–enriched vesicles from rat liver" *J. Cell Biol.* 13(3):523–533.

Yoshimori T et al., 1991, "Bafilomycin $A_1$, a specific inhibitor of vacuolar–type $H^+$–ATPase, inhibits acidification and protein degradation in lysosomes of cultured cells" *J. Biol. Chem.* 266(26):17707–17712.

Dunn WA, 1990, "Studies on the mechanisms of autophagy: maturation of the autophagic vacuole" *J. Cell Biol.* 110:1935–1945.

Sarver N et al., 1990, "Ribozymes as potential anti–HIV–1 therapeutic agents" *Science* 247:1222–1225.

Wang ZQ et al., 1990, "Isolation and Properties of Bovine Kidney Brush Border Vacuolar $H^+$–ATPase" *J. Biol. Chem.* 265(35):21957–21965.

Bowman EJ et al., 1988, "Bafilomycins: A class of inhibitors of membrane ATPases from microorganisms, animal cells, and plant cells" *Proc. Natl. Acad. Sci. USA* 85:7972–7976.

Galloway CJ et al., 1988, "Analysis of endosome and lysosome acidification in vitro" *Methods In Enzymol.* 157:601–611.

Nelson N et al., 1988, "Chromaffin granule proton pump" *Methods In Enzymol.* 157:619–633.

Mains RE et al., 1988, "The role of a low pH intracellular compartment in the processing, storage, and secretion of ACTH and endorphin" *J. Biol. Chem.* 263:(16):7887–7894.

Arai H et al., 1987, "Subunit composition and ATP site labeling of the coated vesicle proton–translocating adenosinetriphosphatase" *Biochemistry* 26:6632–6638.

Wu GY et al., 1987, "Receptor–mediated in vitro gene transformation by a soluble DNA carrier system" *J. Biol. Chem.* 262(10):4429–4432.

Anderson RGW et al., 1984, "Visualization of acidic organelles in intact cells by electron microscopy" *Proc. Natl. Acad. Sci. USA* 81:4838–4842.

Arvan P et al., 1984, "Osmotic properties and internal pH of isolated rat parotid secretory granules" *J. Biol. Chem.* 259(21):13567–13572.

Glickman J et al., 1983, "Golgi membranes contain an electrogenic $H^+$ pump in parallel to a chloride conductance" *J. Cell Biol.* 97:1303–1308.

Revell SH, 1983, "Relationships between chromosome damage and cell death" *Chromosome Damage and Cell Death* pp. 215–233.

Seglen PO et al., 1981, "3–Methyladenine: Specific inhibitor of autophagic/lysosomal protein degradation in isolated rat hepatocytes" *Proc. Natl. Acad. Sci. USA* 79:1889–1892.

O'Farrell PH, 1975, "High resolution two–dimensional electrophoresis of proteins" *J. Biol. Chem.* 250:(10):4007–4021.

* cited by examiner

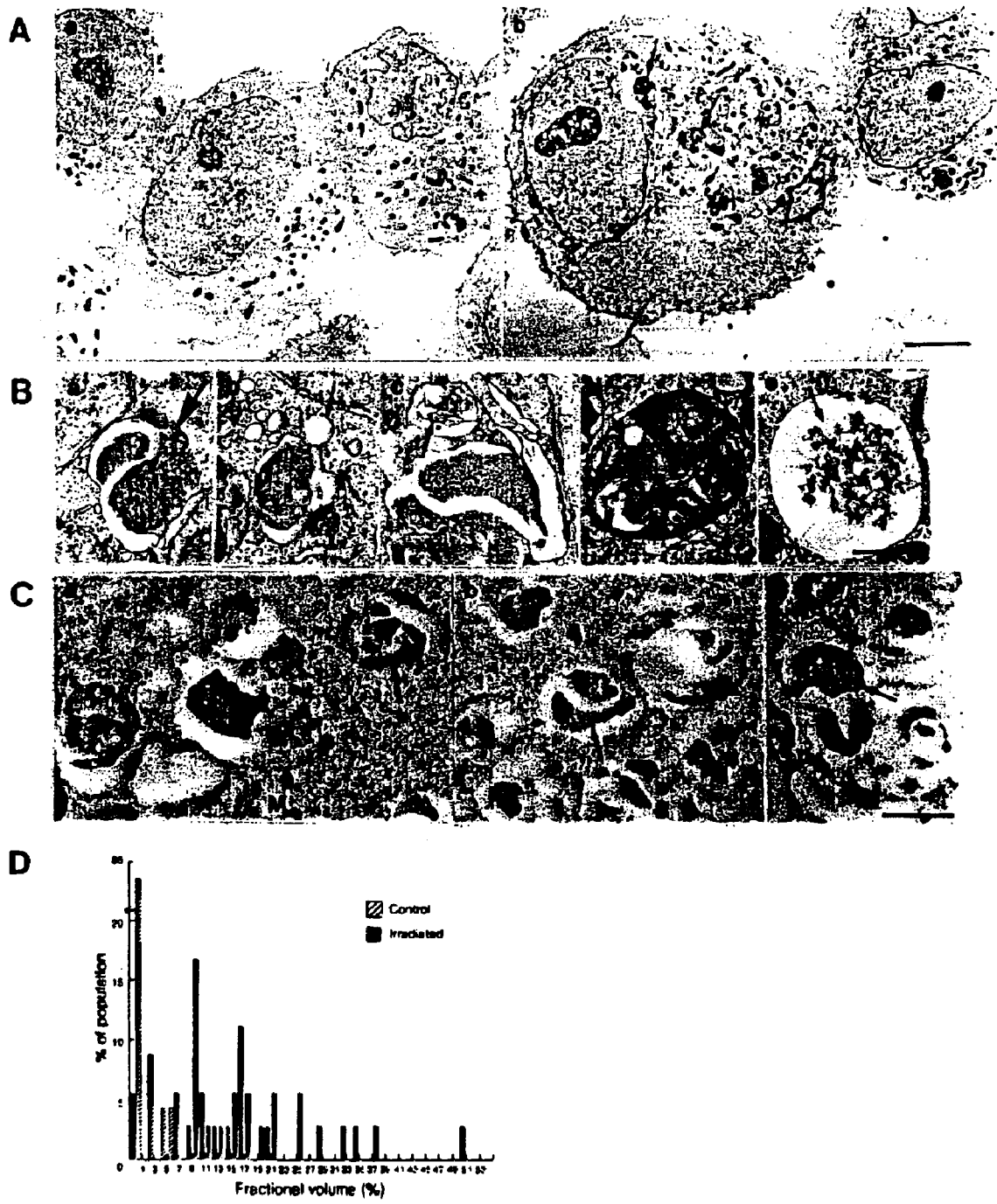
Figure 2A-D

INHIBITION OF VACUOLAR PROTON ATPASE ACTIVITY AND/OR THE MODULATION OF ACIDIC ORGANELLE FUNCTION SENSITIZES CELLS TO RADIATION, CHEMOTHERAPY AND BIOLOGICAL AGENTS

This application is based upon: prior application Ser. No. 60/251,153 filed Dec. 4, 2000, incorporated by reference herein.

The present invention relates to methods and compositions for inhibiting cell survival and/or promoting cell death following exposure to cytotoxic agents and stress such as radiation or chemotherapy exposure through inhibition of V-H$^+$-ATPase. In particular, the formation and/or acidification of acidic vesicular organelles (AVOs) may be prevented or decreased by inhibiting the activity of vacuolar proton ATPase ("V-H$^+$-ATPase"). The methods and compositions of the invention are based on the observation that (i) following irradiation surviving cancer cells accumulate AVOs and that their acidification is mediated by V-H$^+$-ATPase; (ii) surviving colonies of cells contain higher levels of AVOs; and (iii) inhibition of V-H$^+$-ATPase decreases the clonogenic survival of cells irradiated or exposed to chemotherapeutic agents. These observations led to the conclusion that V-H$^+$-ATPase activity and AVO function serve to protect cells from radiation and chemotherapy damage. In addition, agents such as bFGF, TNF-α, PMA, rapamycin and tamoxifen were shown to be inducers of acidic organelle formation. Therefore signal transduction pathways mediated by these agents provide targets for drug screening assays designed to identify inhibitors of V-H$^+$-ATPase activity and AVO formation/acidification. The present invention may be used to treat cancer subjects through sensitization of neoplastic cells to the toxic effects of radiation and chemotherapy.

1. BACKGROUND OF THE INVENTION

The cellular and molecular processes involved in the response of neoplastic epithelial cells to radiation are largely unknown. While in some cell types, particularly of reticuloendothelial origin, death following irradiation is preceded by apoptotic changes, apoptosis plays little or no role in the death of epithelial neoplastic cells following radiation (Bristow et al., 1996, Radiotherapy & Oncol. 40:197–223; Brown et al., 1999, Cancer Res. 59:1391–1399; Finkel, 1999, Science 286:2256–2258). Epithelial cells do not undergo apoptosis following irradiation and are therefore likely to respond with a different sequence of programmed cytoplasmic and nuclear events.

It has been proposed that there are two fundamental mechanisms of cell death (Schwartz et al., 1993, Proc. Natl. Acad. Sci. U.S.A. 90:980–984; Zakeri et al., 1995, Cell Death and Differentiation 2:87–96), referred to as Type I and Type II programmed cell death. Type I programmed cell death, also known as apoptosis, is mediated by a cascade of cysteine aspartases (caspases) and factors released by mitochondria (Reed, 1999, J. Clin. Oncol. 17:2941–2953) and has typical morphological and biochemical characteristics, such as chromatin margination and condensation, early nuclear collapse and nucleosomal ladder formation (Zakeri et al., 1995, Cell Death and Differentiation 2:87–96). In contrast, Type II programmed cell death is marked morphologically by increased autophagy and early destruction of the cytoplasm that either occurs without nuclear collapse or precedes it. Type II programmed cell death has been documented mainly in *Lepidoptera* during metamorphosis and during involution of rat mammary gland (Schwartz et al., 1993, Proc. Natl. Acad. Sci. U.S.A. 90:980–984; Zakeri et al., 1995, Cell Death and Differentiation 2:87–96), but has rarely been associated with stress-inducing stimuli (Bursch et al., 1996, Carcinogenesis 17:1595–1607; Jia et al., 1997, Br. J. Hematol. 98:673–685). Unfortunately, methods for quantification of Type II programmed cell death are lacking, and the molecular mechanisms that regulate it have not been defined.

There are four major classes of ATPases, (i) P-ATPases which use the energy released by ATP hydrolysis to translocate cations across membranes and form a phosphorylated intermediate, i.e., Na+/K+ ATPase; (ii) F-ATPase which utilize energy stored in electrochemical gradient to synthesize ATP, i.e., mitochondrial ATP synthase; (iii) ATP binding cassette (ABC) transporters which mediate efflux of a variety of solutes by hydrolyzing ATP; and (iv) V-ATPase which hydrolyze ATP to create a proton gradient (Lodish, et al., 2000 Molecular Cell buiology ed. S. Tenney Publisher W. H. Freeman and Company).

Vacuolar proton ATPase ("V-H$^+$-ATPase") belongs to a special class of ATPases (V-type) composed of two multi-subunit sectors. The two sectors include a peripheral detachable sector ($V_1$) containing the catalytic ATPase domain and an integral membrane sector ($V_0$) responsible for proton translocation across membranes. The V-H$^+$-ATPase is responsible for acidification of cellular organelles such as endosomes, lysosomes, secretory granules and in some cells the trans-golgi cisternae. Studies with specific inhibitors of the enzyme have shown that maintaining low pH in the acidic compartments is essential for proper vesicular traffic and protein sorting within the cells.

In addition to their role in acidic subcellular organelles, V-ATPases are also found in the plasma membrane of some cancer cells and of specialized cells that specialize in proton secretion such as macrophages, epididymal cells, osteoclasts, renal intercalcalated cells and epididymal cells. In these cells V-ATPases contribute to pH homeostasis, bone resorption and renal acidification (Drose et al,1997, J. Exp. Biology 200:1–8; Gagliardi et al., 1999, Current Medicinal Chemistry 6:1197–1212; Forgac et al 1999).

Specific inhibitors of V-ATPase belong to two major chemical groups the plecomacrolydes (Drose and Altendorf 1997, J. Exp. Biology 200:1–8; Gagliardi et al. 1999, Current Medicinal Chemistry 6:1197–1212) and the benzolactone enamides (Boyd and Farina et al., 2001, J. Pharmacology and Experimental Therapeutics 297:114–120). The most commonly used inhibitors bafilomycins and concanamycins—belong to the first group while the newly discovered salicylihalamide A, lobatamides A-F and oximidines I and II belong to the second group. Bafilomycins and concanamycins are closely related macrolides that possess a six-member hemiacetal ring connected via C3 spacer to a 16 (bafilomycins) or an 18 (concanamycins) member macrocyclic lactone ring. In concanamycins the hemiacetal ring is glycosylated (Drose and Altendorf, 1997, J. Exp. Biology 200:1–8).

Concanamycins and bafilomycins inhibit V-ATPase at nanomolar concentrations. However, they do not affect the activity of F-ATPases and inhibit P-ATPases and ABC transporters only at micromolar concentrations. Therefore, inhibition of an H+-ATPase by nanomolar concentrations of bafilomycins or concanamycins is taken as a criterion for the classification of that enzyme as a V-H+-ATPase (Drose and Altendorf, 1997, J. Exp. Biology 200:1–8). While the IC50 of bafilomycins and concanamycins in in vitro assays is lower than 1 nM, the concentrations needed to affect complete inhibition of acridine orange accumulation by lysosomal compartments in whole cells can reach a few hundreds nanomolar (Drose and Altendorf, 1997, J. Exp. Biology 200:1–8). It has been suggested that because bafilomycins and concanamycins are lipid soluble they may be sequestered in different organelles and thus higher concentrations are required to achieve an effective amount at their targets (Drose and Altendorf, 1997, J. Exp. Biology 200: 1–8).

Bafilomycins and concanamycins are thought to exert their inhibitory effect on V-ATPases by interacting with subunits within its integral membrane complex—Vo, and there is evidence suggesting that the proton channel-forming subunit c and a 116 Kd subunit interact directly with the inhibitors (Drose and Altendorf, 1997, J. Exp. Biology 200:1–8).

Demonstration of V-H$^+$-ATPase-dependent acidification of cellular organelles as well as its involvement in different cellular processes has been achieved by employing the specific inhibitor bafilomycin A1 (Gagliardi, S., et al., 1999, Current Medicinal Chemistry 6:1197–1212). When used at low concentrations (nM range), bafilomycin A1 inhibits V-H$^+$-ATPase activity without affecting the activity of either F or P-type ATPases. However, when bafilomycin A1 is used at the $\mu$M range F and P-type ATPases activities are affected.

Several studies reported that long-term incubation of cultured cells with bafilomycin A1 resulted in cell death (Drose and Altendorf 1997; Gagliardi, Rees et al. 1999). Additionally, a concomitant inhibition of V-H$^+$-ATPase with bafilomycin A1, and of Na$^+$/H$^+$ antiporter with 5-(N-ethyl-N-isopropyl)-amiloride in human breast cancer cells results in decreased cytoplasmic pH and increased DNA degradation (Thangara, M., Cancer Research 59:1649–1654). However, Manabe et al. (Manabe et al., 1993 J. Cell Physiol 157:445–452) claim that removal of the compound following short-term incubation resulted in resumption of cell growth. Because bafilomycin A1 binds tightly to V-ATPase (KD 10$^{-8}$ mol./l), the reversibility of the effect was attributed to de novo synthesis of the enzyme (Drose and Altendorf, 1997, J. Exp. Biology 200:1–8).

At concentrations greater than 10 nM bafilomycin A1 was reported to induce apoptosis in Capan-1 human pancreatic cancer cell line in vitro. Subcutaneous administration of doses smaller than 1 mg/kg/day did not affect the growth of nude mice for up to four weeks, and based on histological examination did not affect the liver, pancreas, small intestine, kidney or lung during the four weeks treatment. However, such treatment caused apoptotic death of Capan-1 cells in their xenograft tumor and overall shrinkage of the tumors (Ohta et al., 1998 Journal of Pathology 185:324–340).

When injected intravenously bafilomycin A1 is toxic (Keeling, 1997, Ann. N.Y. Acad Science 834:600–608). However, when administered subcutaneously bafilomycin A1 is tolerated. Doses of 1.4 mol/kg/day for 14 days were non-toxic and increased bone readsorption.

Unlike bafilomycins and concanamycins that inhibit V-ATPase from animal cells as well as from fungi and yeast, benzolactone enamides inhibit V-ATPase from animal cells alone. These compounds do not inhibit F-ATPases or P-ATPases and exert their effect on V-ATPases at the nanomolar range. Again, their inhibitory effect on the enzyme activity in vitro was exerted at lower concentrations (IC50<1 nM) than their effect on cell proliferation (IC50~10 nM to a few hundreds nM) (Boyd and Farina et al., 2001, J. Pharmacology and Experimental Therapeutics 297:114–120).

Radiation and chemotherapy play an important role in treatment of many different types of cancers due to the preferential destruction of rapidly dividing cells by exposure to radiation or anticancer agents. However, such treatment can also destroy normal cells which reproduce rapidly such as skin, hair follicles, lining of the intestines and blood element generating components in the bone marrow. Destruction of such normal cells leads to undesirable side effects, which include nausea or vomiting, low blood cell counts (with consequent susceptibility to infections and risk of hemorrhage) and loss of hair. Therefore, improvements in radiation and chemotherapies designed to sensitize neoplastic cells or protect normal cells from the toxic effects of radiation or chemotherapy are highly desirable.

2. SUMMARY OF THE INVENTION

The present invention is based, at least in part, on the discoveries that (i) following irradiation surviving cancer cells accumulate acidic vesicular organelles (AVOs) and that their acidification is mediated by V-H$^+$-ATPase; (ii) surviving colonies of cells contain higher levels of AVO; and (iii) inhibition of V-H$^+$-ATPase decreases the clonogenic survival of cells irradiated or exposed to chemotherapeutic agents. These observations indicate that V-H$^+$-ATPase activity and mediation of AVO function/acidification is required for cell survival following irradiation or exposure to chemotherapeutic agents. The data presented herein demonstrates that small concentrations of V-H$^+$-ATPase inhibitors that would normally not be sufficient to affect cell survival, enhance cell sensitivity to radiation and chemotherapeutic agents.

Accordingly, the present invention provides for methods of inhibiting cell survival and/or promoting cell death comprising inhibiting V-H$^+$-ATPase activity and the function/ acidification of AVOs following exposure to radiation or chemotherapy. In particular, the acidification of AVOs may be prevented or decreased by inhibitors of V-H$^+$-ATPase, such as, but not limited to, macrolides such as bafilomycin A1 and concanamycin and benzolactone enamides such as salicilyhalamide A, lobatamide A and oximidine II. Lysosomotropic agents are also candidate modulators of AVO function as well as antisense molecules designed to prevent AVO formation and/or the expression of V-H$^+$-ATPase subunits within the cell.

In addition, as described herein, a number of different compounds were discovered to be inducers of acidic organelle formation. Such compounds include bFGF, TNF, PMA and tamoxifen. The discovery that such compounds are capable of inducing acidic organelle formation indicate that components of the signal transduction pathway mediated by these compounds can provide targets for drug screening assays designed to identify inhibitors of acidic organelle formation.

The yeast protein TOR (target of rapamycin) is known to be a negative modulator of autophagy. The immunosuppressant drug rapamycin forms a complex with FKBP12 and TOR and inhibits enzyme activity. Inhibition of the human analog of TOR (mTOR) with the immunosuppressant drug rapamycin was found to lead to AVO formation in cancer cells. Thus, methods and compounds designed to modulate mTOR activity may be utilized to alter the sensitivity of cells to radiation or chemotherapeutic exposure.

Other compounds that may be used in the practice of the invention include modulators of phosphatidylinositol 3'-kinase activity. Of particular interest are modulators of class III phosphatidylinositol 3'-kinases, whose product phosphatidylinositol 3-phosphate stimulates autophagy (Petiot et al., 2000, J. Biol. Chem. 275:992–998). The use of such compounds is based on the discovery that modulators such as 3-methyladenine (3-MA), an inhibitor of class III phosphatidylinositol 3'-kinase, inhibited AVO formation following irradiation. Thus, class III phosphatidylinositol 3'-kinase inhibitors may also be utilized to inhibit AVO formation and V-H$^+$-ATPase activity thereby modulating cellular sensitivity to radiation and chemotherapy.

Proteins that are responsible for the execution of different stages in macroautophagy, i.e., sequestration, fusion between vacuoles, have been discovered in yeast and their corresponding mammalian homologues have been identified. Such proteins include hApg5p and hApg12p (Kim, J. and Klionsky D J, Ann. Rev. Biochem. 69:303–342). In an embodiment of the invention modulators of such proteins, including but not limited to antisense molecules designed to inhibit the expression of such proteins, may be used to modulate the function and/or acidification of AVO.

One of the advantages of the present invention is that, by sensitizing cells to the damaging effects of radiation or chemotherapy, it permits lower doses of radiation to be therapeutically effective. Absent such a sensitizer, relatively high doses of radiation or chemotherapy are required to effect cancer cell death. Such high doses tend to be toxic to normal tissues as well. Use of a radiosensitizer or chemosensitizer therefore diminishes unwanted damage to normal tissues.

3. BRIEF DESCRIPTION OF THE FIGURES

Figure 1B:
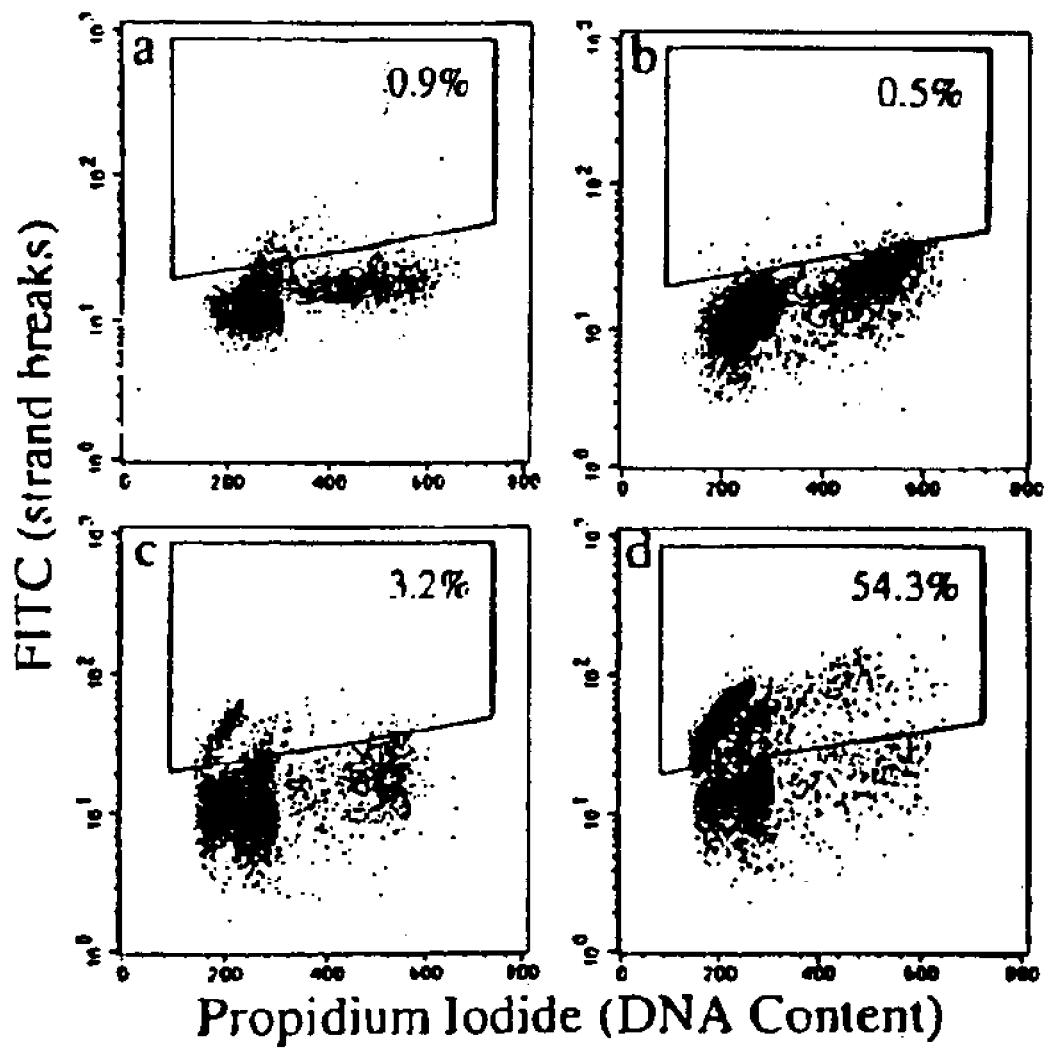

FIGS. 1A–B. Biochemical apotoic hallmarks were not detected in irradiated MCF-7 cells. FIG. 1A. Irradiated cells showing non-discrete DNA degradation (+), and control unirradiated (−) cells were harvested at the noted time post-T0 (irradiation time). E—endothelial cells treated with $H_2O_2$. M—lambda DNA/Hind III markers. FIG. 1B. MCF-7 and endothelial cells were treated as above and processed for the TUNEL procedure 48 hours following irradiation. (a) Control MCF-7, (b) irradiated MCF-7, (c) untreated endothelial cells, (d) $H_2O_2$ treated endothelial cells.

FIGS. 2A–D. Ultrastructure of acidic organelles formed in irradiated cells. FIG. 2A. (a) control unirradiated cells 48 hours post-irradiation time (T0). (b) Cells irradiated with 10 Gy 48 hours post-irradiation. The arrow points to newly formed vesicular organelles. Bar (a–b): 4 $\mu$M. FIG. 2B. Newly formed vesicular organelles in cells irradiated as above. The arrows point to the part-rough part-smooth membrane cisternae (a), to vesicles fusing with membrane cisternae (b), to lamellar structures (c,d) and to residual digested material (e). Bar (a–e) 0.6 $\mu$M. FIG. 2C. Concentration of the lysosomotropic agent DAMP in acidic organelles (AVO-EM) demonstrated by immunogold histochemistry. Cells were stained with DAMP 24 hours post-irradiation with 10 Gy and processed for viewing as described in methods. The arrow points to the gold particles over the acidic organelles (a). Cells were incubated with 0.5 $\mu$M bafilomycin A1 (b) or 300 $\mu$M chloroquine (c) prior to addition of DAMP. Bar (a–c): 0.6 $\mu$M. FIG. 2D. Distribution of unirradiated and irradiated cell populations according to the fraction of the cytoplasmic volume occupied by AVO-EM (fractional volume).

Figure 3A:
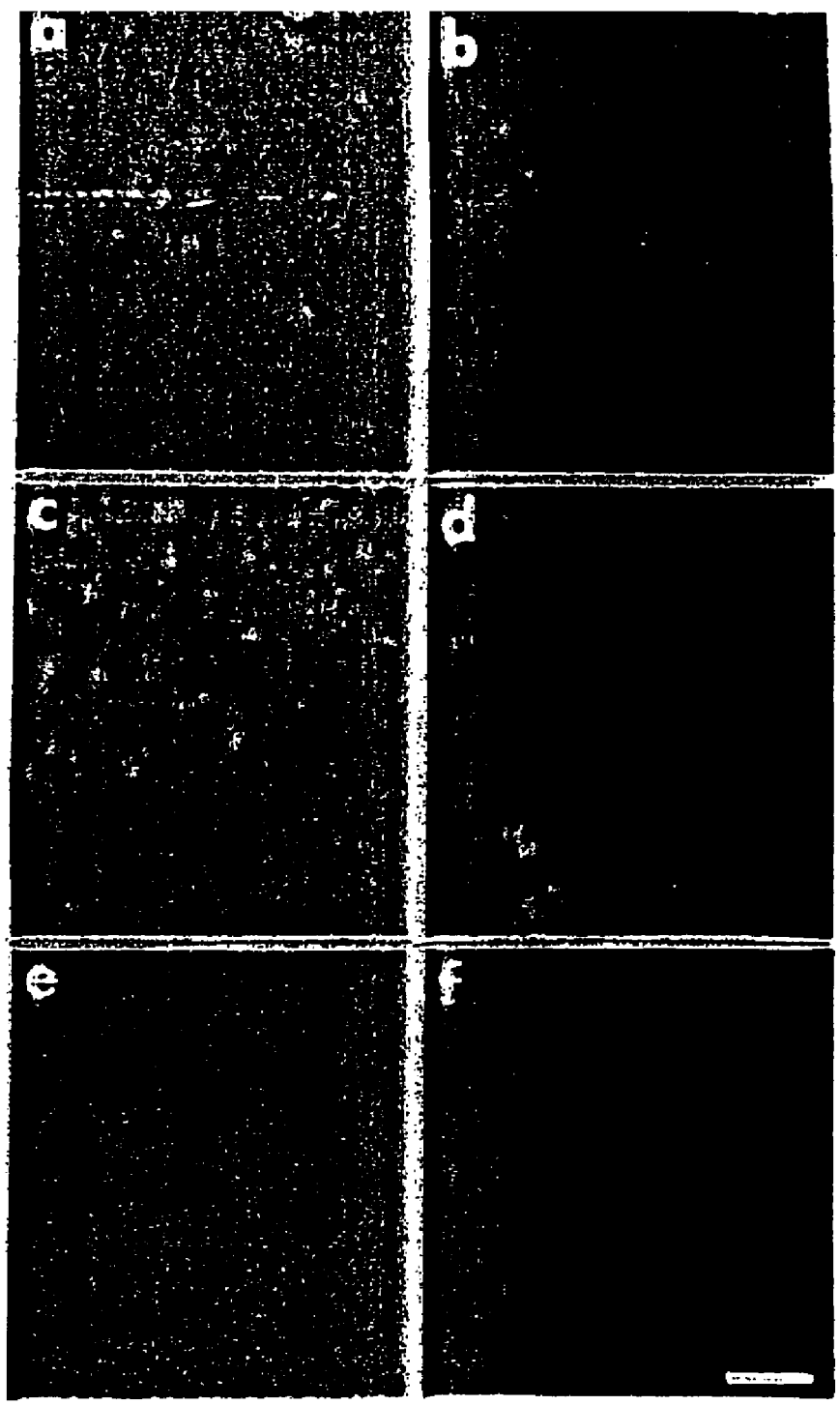

FIG. 3A. Detection of radiation induced appearance of AVO by vital staining with lysosomotropic agents. Acridine orange: (a,c) Unirradiated cells, (b,d) 30 hours following irradiation with 10 Gy, (c,d) Cells were incubated with 200 nM bafilomycin A1 for 30 minutes prior to addition of acridine orange. LysoSensor Blue DND-167: (e) Unirradiated cells and (f) cells 30 hours following exposure to 10 Gy. Bar: 18 $\mu$M.

Figure 3B:
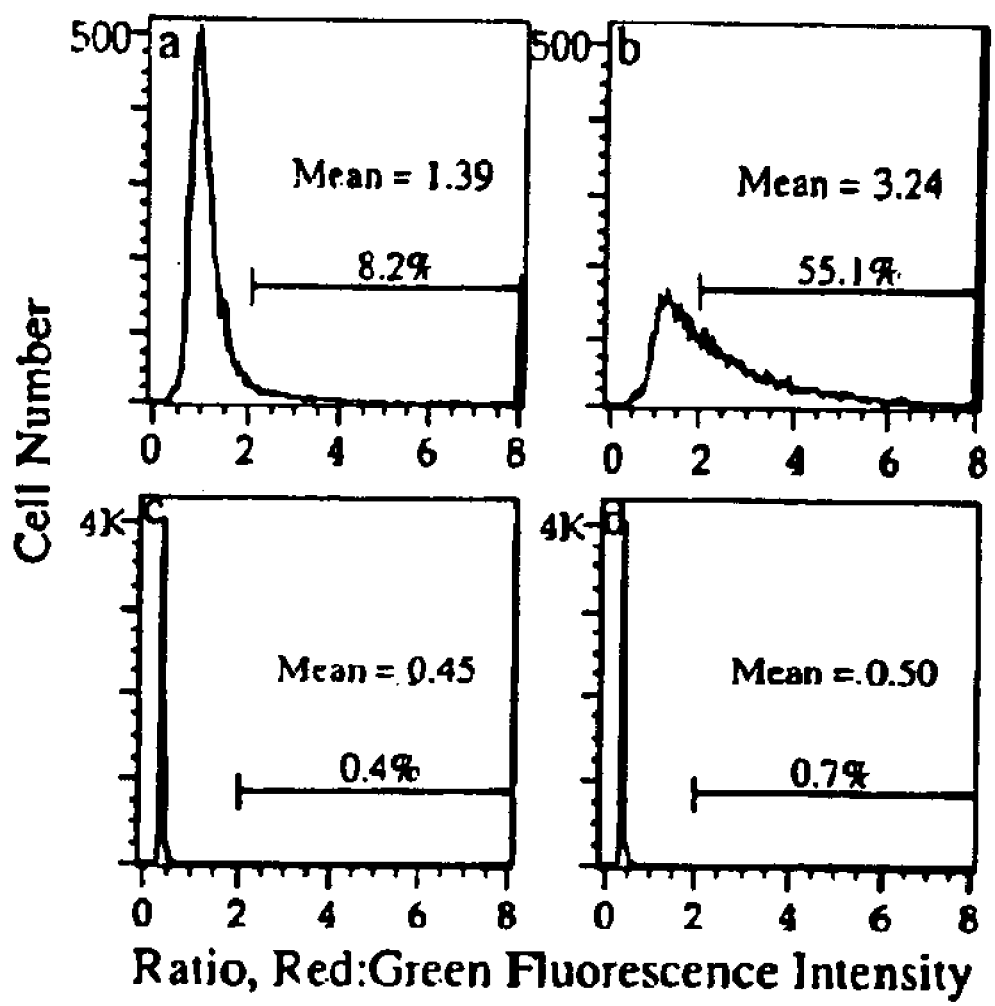

FIG. 3B. Determination of mean red/green fluorescence ratio in acridine orange stained cells using flow cytometry. The mean red to green fluorescence ratio in irradiated and control unirradiated cells was determined. (a,c) unirradiated cells, (b,d) cells 24 hours following irradiation with 10 Gy, (c,d) unirradiated and irradiated cells pre-incubated with 500 nM bafilomycin A1 30 minutes prior to addition of acridine orange.

Figure 4:
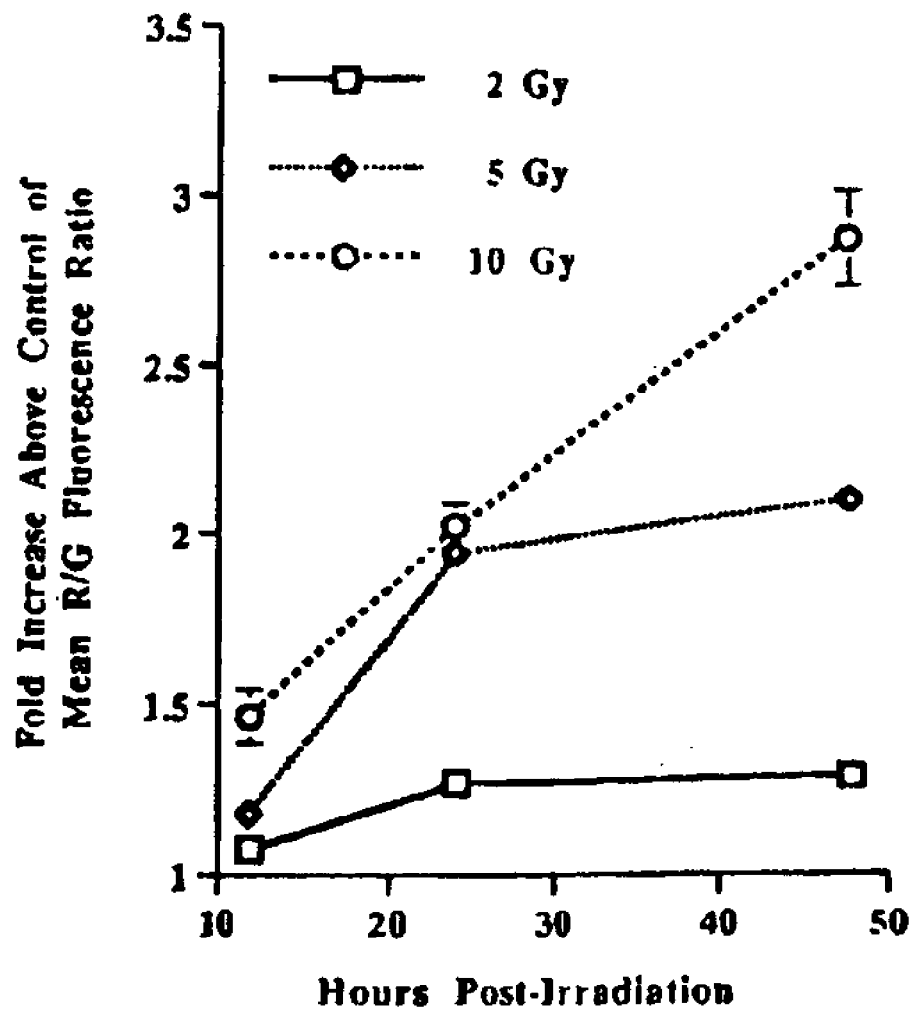

FIG. 4. Increased red to green (R/G) fluorescence ratio in irradiated cells is radiation dose and time-dependent. Cells were stained and processed for flow cytometric analysis. The numbers represent fold increase of red to green fluorescence ratio in irradiated cells above controls, and are the mean±S.D. of triplicate samples from one experiment that was reproduced twice with similar results.

Figure 5A:
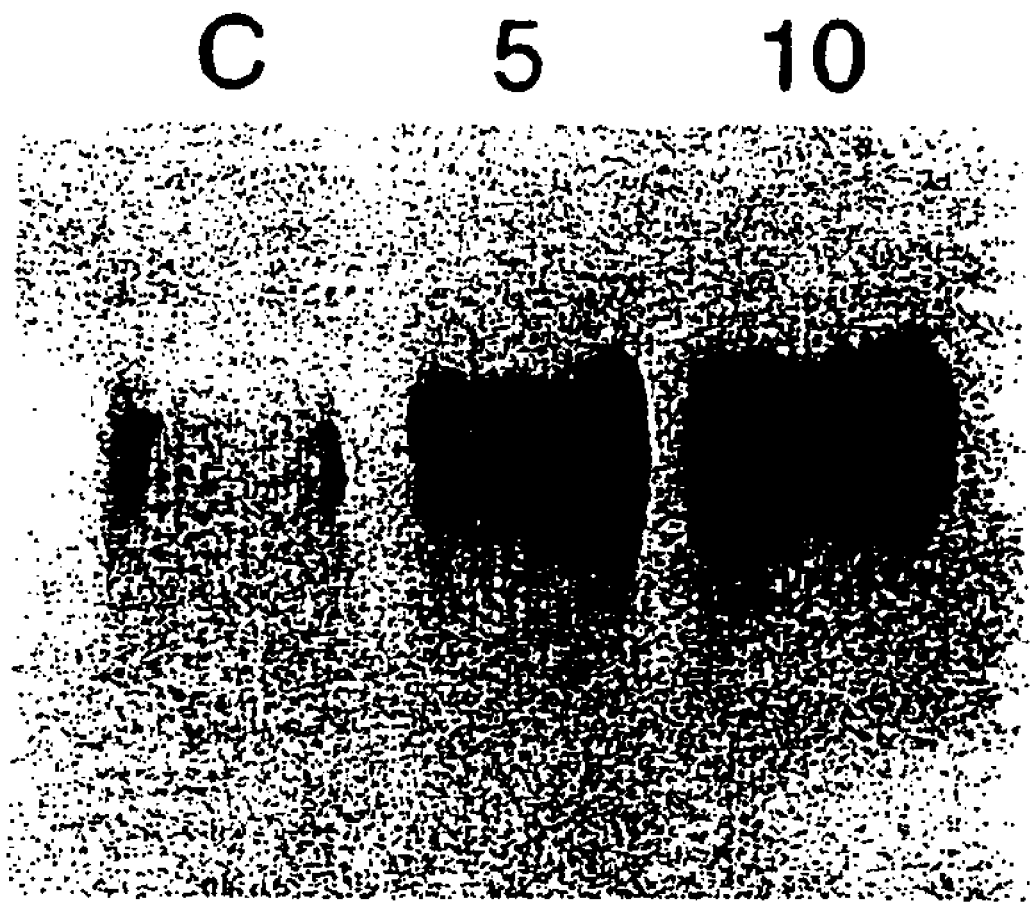
Figure 5B:
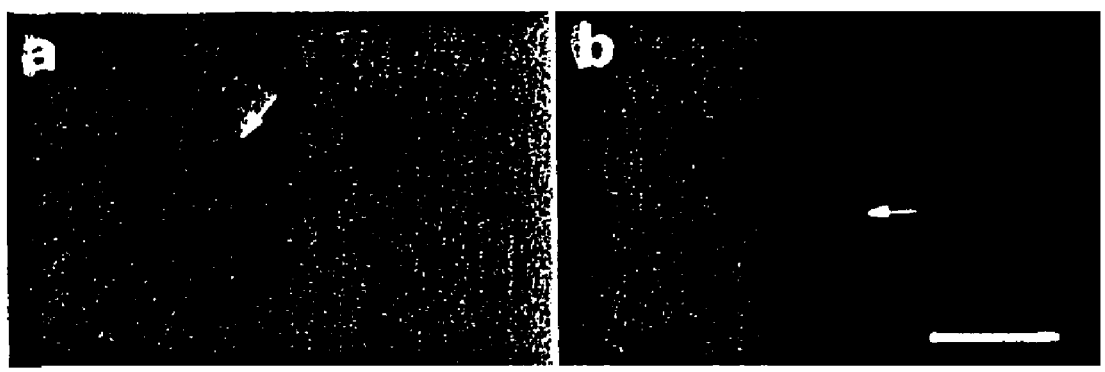

FIG. 5. Radiation induces increase in LAMP-1 levels. FIG. 5A. Western blotting analysis of LAMP-1. Cells were harvested 48 hours following irradiation with 10 Gy. Equal amounts of cell lysates from control and irradiated cells were analyzed for LAMP-1 content. C. control unirradiated cells. 5. Cells irradiated with 5 Gy. 10. Cells irradiated with 10 Gy. FIG. 5B. Immunolocalization of LAMP-1 in control and irradiated cells: The staining showed the increased levels of LAMP-1 in the cells at 48 hours following irradiation and its localization to vesicular bodies. (a) Unirradiated cells. (b) Cells irradiated with 10 Gy.

Figure 6:
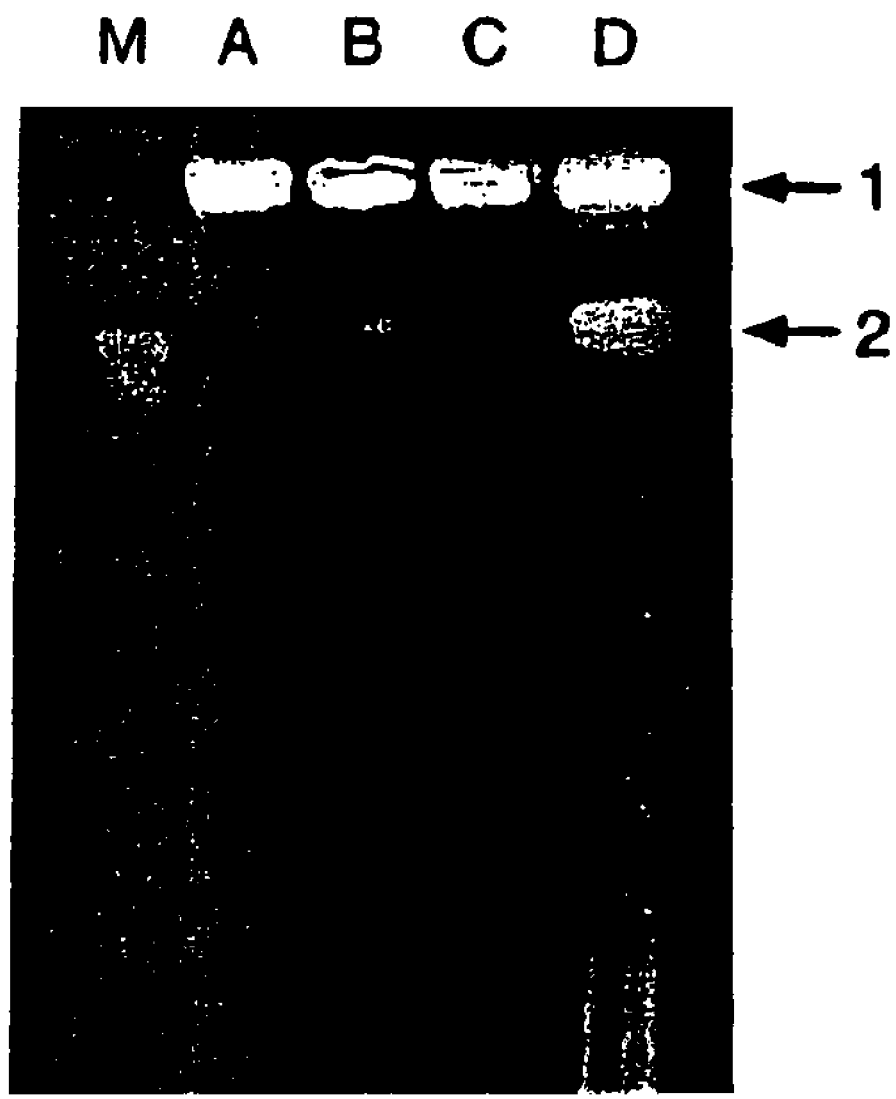

FIG. 6. Bafilomycin A1 enhances DNA fragmentation in irradiated cells: Cells were irradiated 48 hours post-plating and bafilomycin A1 (4 nM) was added 48 hours following irradiation, for the duration of 24 hours, from concentrated stock solution at dimethylsulfoxide (DMSO) to a final concentration of 4 nM. Control cells received the vehicle alone. Cells were harvested 72 hours following irradiation. Plug preparation and resolution of DNA was conducted according to Gilles et al. (2000, Blood 95:2930–2936). M-DNA size standard, lambda 50 kb ladder. A-Unirradiated controls. B-Cells irradiated with 10 Gy. C-Unirradiated cells incubated with 4 nM bafilomycin A1. D-Cells irradiated with 10 Gy and incubated with 4 nM bafilomycin A1. Window of DNA resolution was 20 kb–1000 kb. Arrow 1 points to sample origin. Arrow 2 points to zone of no resolution.

Figure 7:
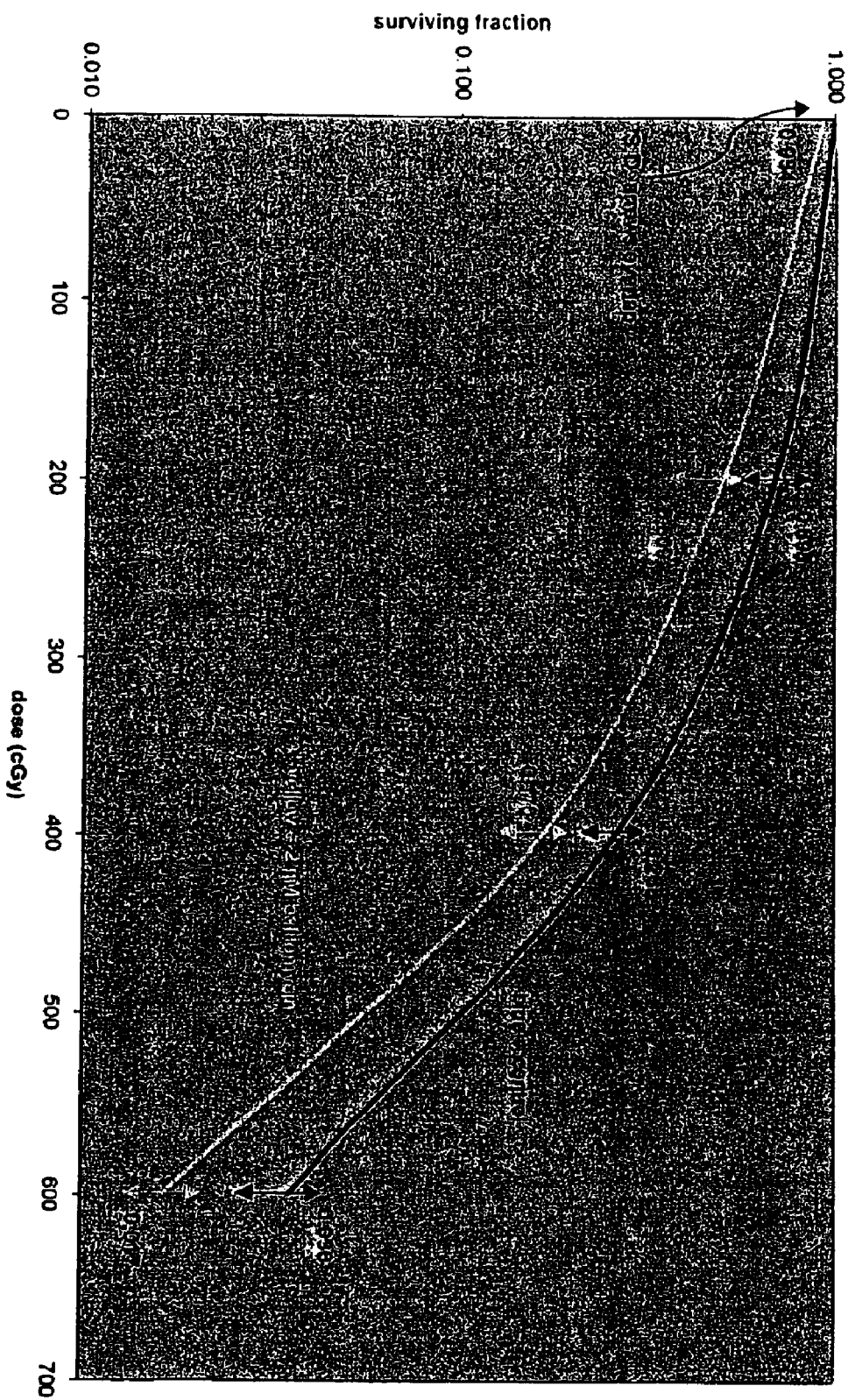

FIG. 7. The effect of 2 nM bafilomycin A1 on the clonogenic survival of irradiated human breast cancer cells.

Figure 8:
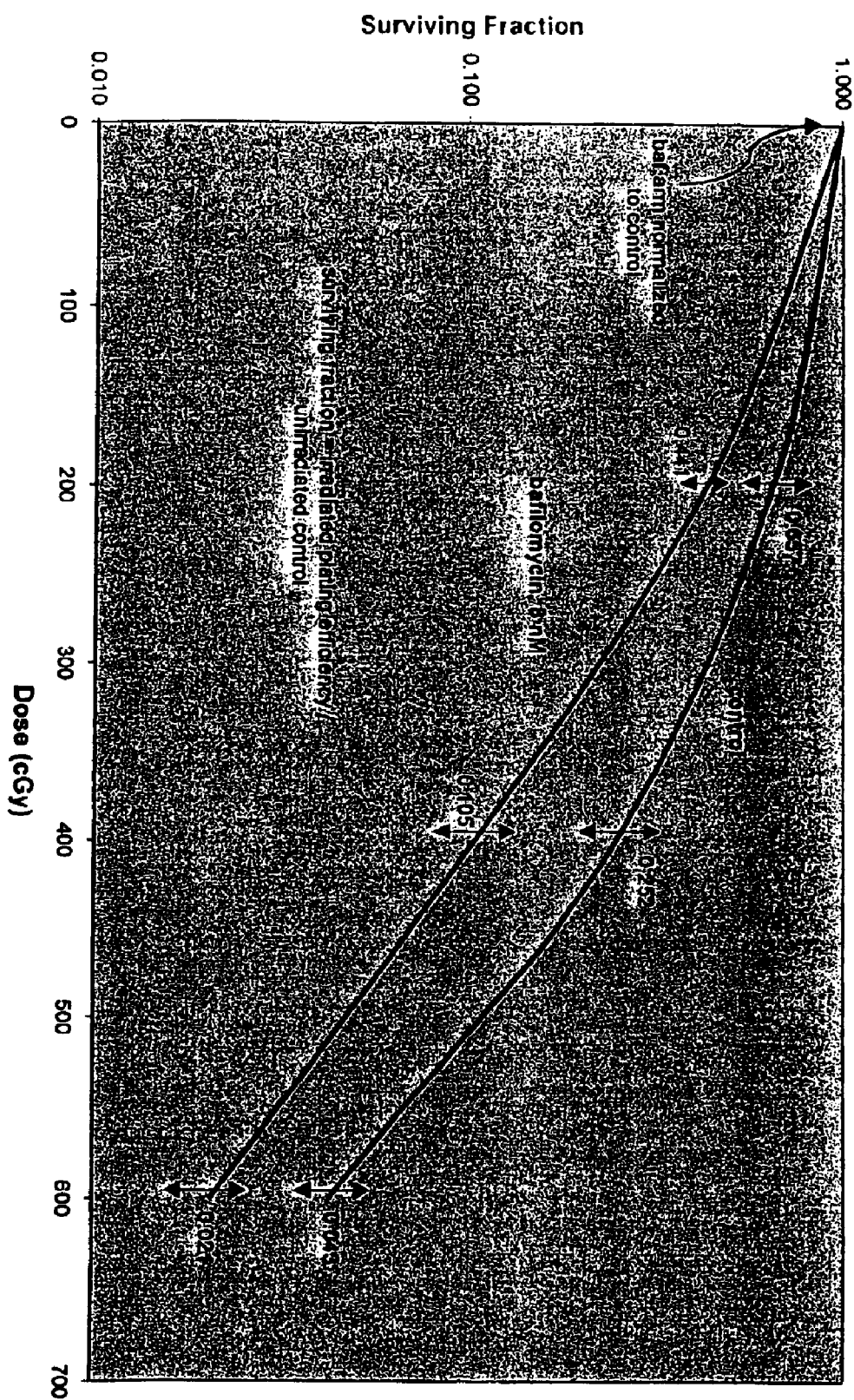

FIG. 8. The effect of 8 nM bafilomycin A1 on the clonogenic survival of irradiated human breast cancer cells.

Figure 9:
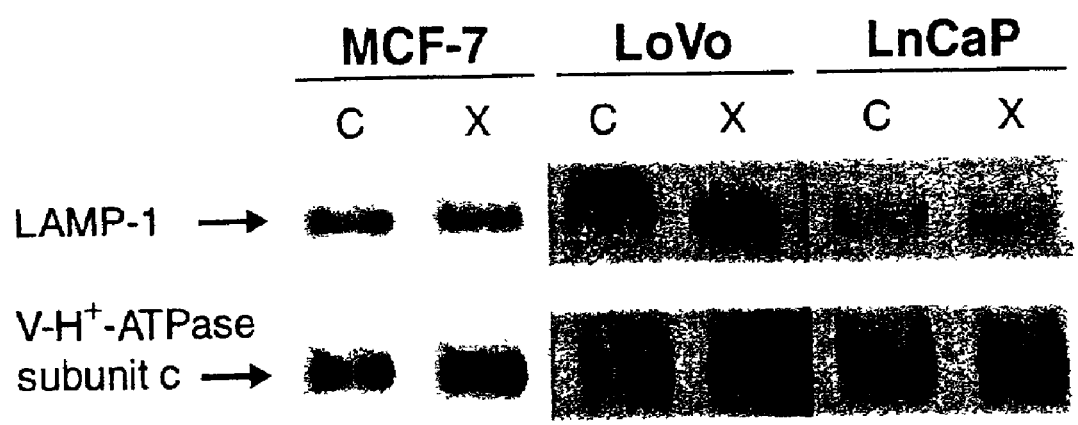

FIG. 9. Radiation induces an increase in mRNA level for subunit c of the V-H$^+$-ATPase. MCF-7 (human breast adenocarcinoma), LoVo (human colon adenocarconoma) and LNCaP (human prostate carcinoma) where either unirradiated (C) or irradiated with 10 Gy (X). Note that levels of LAMP mRNA remain unchanged.

5. DETAILED DESCRIPTION OF THE INVENTION

The present invention provides for methods of inhibiting cell survival and/or promoting cell death comprising inhibiting V-H$^+$-ATPase activity and/or the function/acidification of AVO. The present invention further provides for assays designed to identify compounds capable of modulating V-H$^+$-ATPase activity and/or the function/acidification of AVO following exposure to cytotoxic agents. Such assays include an acridine orange accumulation assay capable of detecting changes in the acidification of vacuolar vesicles. The present invention further relates to methods for increasing the sensitivity of neoplasic cells to radiation or chemotherapy exposure in cancer subjects through administration of compounds capable of modulating V-H$^+$-ATPase activity and/or function/acidification of AVO.

5.1 V-H$^+$-ATPase Activity and Acidic Organelle Function Protect Against Radiation Damage The present invention is based, at least in part, on the discovery that irradiation of cancer cells results in the appearance and accumulation of acidic vesicular organelles ("AVO") and that acidification of AVO is decreased by V-H$^+$-ATPase inhibitors. Such inhibitors also promote the damaging effects of radiation and chemotherapy and result in greater cell death than radiation or chemotherapy alone. Specifically, it was observed that the progeny of irradiated cells contain increased levels of AVO indicating that the emergence of acidic compartments serve to protect cells against radiation damage. Further, inhibition of V-H$^+$-ATPase acidification by bafilomycin A1 was found to result in enhanced DNA degradation and decreased clonogenic survival following irradiation and chemotherapy.

Inhibition of V-H$^+$-ATPase activity resulted in enhanced DNA degradation with the effect being most pronounced when formation of large non-discrete DNA fragments (20 kb–1000 kb) were detected using pulse field gel electrophoresis (PFGE). The effect of bafilomycin A1 on radiosensitivity is best demonstrated at 2 nM. At this concentration bafilomycin A1 reduces the survival of irradiated cells without significantly affecting the survival of unirradiated cells. In two separate experiments 2 nM bafilomycin A1 reduced the survival of cells irradiated with 300 cGy by 45% and 32%. The effect of the inhibitor at that low concentration on the clonogenic survival curve is shown in FIG. 7 and Table 2, 4–7. Increasing the concentrations of bafilomycin A1 to 8 nM enhanced its radiosensitizing effect, however at that concentration bafilomycin A1 also decreased the survival of the unirradiated cells (FIG. 8 and Table 3). The effect of bafilomycin A1 on cellular radiosensitivity was also demonstrated with irradiated colon adenocarcinoma (LoVo) cells (Table 11–13).

Increased autophagy, the hallmark of programmed cell death type II, is thought to lead to cell death via destruction of the cytoplasm. However, the results described herein demonstrate that accumulation of acidic organelles following irradiation is modulated by cellular defense mechanisms, namely, the moderate formation of AVO in surviving colonies provide long-term protection against low radiation damage. However, continuous accretion of AVO following high level of damage may offset their protective effect, leading to replacement of the normal cytoplasm and possibly to necrosis and cell death. These organelles may protect the cells by preventing cytoplasmic acidification, by providing catabolites required for repair processes, and/or by containing toxic molecules. Thus, inhibitors of AVO function/acidification may be utilized to increase cell death following low radiation damage.

The present invention is also based on the discovery that inhibition of AVO acidification by bafilomycin A1, or in some instances salicilyhalamide A was found to result in decreased clonogenic survival following exposure of cancer cells to chermotherapeutic agents such as adriamycin and etoposide (Table 14–19).

Additionally, it was discovered that a number of additional agents were capable of inducing the accumulation of acidic organelles within cancer cells. For example, a number of different cytokines and known modulators of enzymatic activities in cells increased the content of acidic organelles in cells (Table 20–23). For example, using the acridine orange assay described herein, it was discovered that bFGF, TNF, PMA, rapamycin and tamoxifen were capable of inducing the accumulation of acidic organelles. The identification of compounds capable of modulating the accumulation of acidic organelles provides insight into the signal transduction pathways involved in such accumulation and provides targets for drug screening assays designed to identify compounds capable of increasing the sensitivity of cancer cells to radiation therapy or chemotherapy.

Modulation of V-H$^+$-ATPase and AVO function/acidification may prove useful for increasing the therapeutic ratio of radiation treatment of epithelial cancers. In addition, since accumulation of acidic organelles have been reported in cells treated with chemotherapeutic agents and in pathological conditions such as Parkinson's disease and Alzheimer's disease, compounds that modulate the biogenesis and function of acidic organelles may be used in conjunction with other types of cancer treatment or to treat other diseases associated with acidification of acidic organelles.

5.2 Compounds Useful in Modulating the Activity of V-H$^+$-ATPase Activity and AVO Function/Acidification The present invention provides for methods and compositions for decreasing cell survival and/or promoting cell death comprising inhibiting V-H$^+$-ATPase activity and/or function/acidification of AVO, particularly after exposure of the cells to a cytotoxic agent. The cytotoxic agent may be radiation, including x-ray irradiation and particle emission (e.g. from a radioactive seed) or a chemical agent, such as a chemotherapeutic agent used in cancer treatment (adriamycin or etoposide, for example) or hormones such as tamoxifen or other biologicals such as TNF-α or bFGF. The present invention is based, at least in part, on the discovery that irradiation of cancer cells results in the appearance and accumulation of acidic vesicular organelles, i.e., AVO, which are acidified by a V-H$^+$-ATPase. Inhibition of acidification of these organelles by inhibition of V-H$^+$-ATPase promotes the damaging effects of the radiation and results in greater cell death than radiation alone.

In addition, it was discovered that inhibition of V-H$^+$-ATPase activity resulted in an increase in cell death mediated by exposure of the cells to chemotherapeutic agents such as adriamycin and etoposide (Table 14–19).

Accordingly, the present invention provides for methods of inhibiting cell survival and/or promoting cell death comprising inhibiting V-H$^+$-ATPase activity and/or the function/acidification of AVOs. In particular, the acidification of AVOs may be prevented or decreased by inhibitors of V-H$^+$-ATPase, such as, for example, macrocyclic lactone compounds such as bafilomycin A1 and concanamycin and compounds belonging to the group of benzolactone enamides such as salicylihalamide A. In addition, the invention provides methods of inhibiting cell survival and/or promoting cell death comprising inhibiting components of the signal transduction pathway that normally leads to an increase in organelle acidification.

One of the advantages of the present invention is that, by sensitizing cells to the toxic effects of radiation or chemotherapy, it permits lower doses of radiation or chemotherapy to be therapeutically effective. Absent such a sensitizer, relatively high doses of radiation or chemotherapeutic agents are required to effect cancer cell death. Such high doses tend to be toxic to normal tissues as well. Use of a radiosensitizer or chemosensitizer therefore diminishes unwanted damage to normal tissues.

The present invention provides for compositions comprising compounds that inhibit AVO formation and function as well as inhibitors of V-H$^+$-ATPase activity. The degree of inhibition required to modulate radiosensitivity or chemosensitivity of cells can be determined experimentally using routine methods such as clonogenic assays and xenograft animal models.

In preferred embodiments of the invention, the V-H$^+$-ATPase inhibitor is bafilomycin A1, having the following structure:

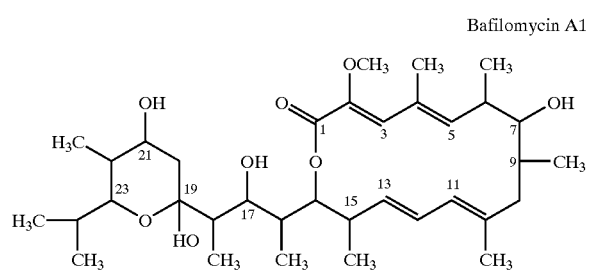

Bafilomycin A1

In addition, compounds including but not limited to (i) macrocyclic lactone antibiotics such as concanamycin and benzolactone enamides such as salicylihalamide A; (ii) inhibitors of the rapamycin, bFGF, TNF-α, PMA and the class III phosphatidylinositol 3'-kinase signal transduction pathway; and (iii) antisense nucleic acid molecules designed to inhibit the expression of V-H$^+$-ATPase and/or autopaghy pathway genes may be used to increase the sensitivity of cells to radiation or chemotherapy.

5.2.1. Non-Cell Based Screening Assays for Compounds Useful in Modulating the Activity of V-H$^+$-ATPase In accordance with the invention, non-cell based assay systems may be used to identify compounds that interact with, i.e., bind to V-H$^+$-ATPase, and regulate the enzymatic activity of V-H$^+$-ATPase. Such compounds may act as antagonists or agonists of V-H$^+$-ATPase activity and may be used to regulate cellular sensitivity to radiation or chemotherapeutic exposure. Recombinant V-H$^+$-ATPase, peptides corresponding to different functional domains or subunit fusion proteins may be expressed and used in assays to identify compounds that interact with V-H$^+$-ATPase.

To this end, soluble regions of V-H$^+$-ATPase may be recombinantly expressed and utilized in non-cell based assays to identify compounds that bind to V-H$^+$-ATPase. Recombinantly expressed V-H$^+$-ATPase polypeptides or fusion proteins containing one or more of the V-H$^+$-ATPase functional domains may be prepared using techniques well known to those of skill in the art, and used in the non-cell based screening assays. For example, a soluble truncated V-H$^+$-ATPase polypeptide, a peptide corresponding to a functional domain, or a fusion protein containing a V-H$^+$-ATPase protein domain fused to a protein or polypeptide that affords advantages in the assay system (e g, labeling, isolation of the resulting complex, etc.) can be utilized.

The V-H$^+$-ATPase may also be one which has been fully or partially isolated from cell membranes, or which may be present as part of a crude or semi-purified extract. As a non-limiting example, the V-H$^+$-ATPase protein may be present in a preparation of cell membranes. In particular embodiments of the invention, such cell membranes may be prepared using methods known to those of skill in the art. Preparations of solubilized and highly enriched enzyme can also by prepared using the methods of Arai et al. (1987, Biochemistry 26:6632–6638) and Yeh, (1991, Hepatology 13:523–533).

The principle of the assays used to identify compounds that bind to V-H$^+$-ATPase involves preparing a reaction mixture of the V-H$^+$-ATPase and the test compound under conditions and for time sufficient to allow the two components to interact and bind, thus forming a complex which can be removed and/or detected in the reaction mixture. The identity of the bound test compound is then determined.

The screening assays are accomplished by any of a variety of commonly known methods. For example, one method to conduct such an assay involves anchoring the V-H$^+$-ATPase protein, polypeptide, peptide, fusion protein or the test substance onto a solid phase and detecting V-H$^+$-ATPase/test compound complexes anchored on the solid phase at the end of the reaction. In one embodiment of such a method, the V-H$^+$-ATPase reactant is anchored onto a solid surface, and the test compound, which is not anchored, may be labeled, either directly or indirectly.

In practice, microtitre plates conveniently can be utilized as the solid phase. The anchored component is immobilized by non-covalent or covalent attachments. The surfaces may be prepared in advance and stored. In order to conduct the assay, the non-immobilized component is added to the coated surfaces containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the solid surface; e.g., using a labeled antibody specific for the previously non-immobilized component.

Alternatively, a reaction is conducted in a liquid phase, the reaction products separated from unreacted components using an immobilized antibody specific for V-H$^+$-ATPase protein, fusion protein or the test compound, and complexes detected using a labeled antibody specific for the other component of the possible complex to detect anchored complexes.

In accordance with the invention, non-cell based assays may also be used to screen for compounds that directly inhibit the enzymatic activity associated with V-H$^+$-ATPase, i.e., ATPase activity. To this end, a reaction mixture of V-H$^+$-ATPase and a test compound is prepared in the presence of substrate and the enzymatic activity of V-H$^+$-ATPase is compared to the activity observed in the absence of test compound. Substrates that may be used in the assays for detection of V-H$^+$-ATPase enzyme activity include but are not limited to ATP and labeled forms thereof.

V-H$^+$-ATPase enzyme activity can be determined utilizing, for example, membrane preparations comprising V-H$^+$-ATPase. Sources of AVO include yeast vacuoles, bovine chromaffine granules as well as subcellular fractions of AVO and gradient-purified V-H$^+$-ATPase derived from mammalian cell lines such as MCF-7, to name a few. In addition, membrane vesicles enriched with V-ATPase have been isolated from a variety of mammalian tissues. For example, stripped coated vesicles from bovine brain (Arai et al., 1987, Biochemistry 26:6632–6638), Golgi vesicles from rat liver (Glickman et al. 1983; J. Cell Biol. 97:1303–1308 Yeh et al., 1991, Hepatology 13:523–533), chromaffin granules from bovine adrenals (Nelson et al. 1988, Methods in Enzymology, Fleischer and Fleischer. San Diego, New York, Academic Press Inc., 157:601–611), and brush border membrane from bovine kidney (Wang and Gluck, 1990 J. Biol. Chem 265:21957–21965) have been isolated. In a preferred embodiment of the invention, membrane preparations from human liver or kidney tissue as well as from membrane form human osteoclast canbe prepared (Boyd and Paull, 1995 Drug Dev. Res. 34:91–109).

The enzymatic activity can be monitored by a coupled-enzyme-ATP regeneration system as described in Roberts et al., (Methods of Enzymol. 194:644–661). V-ATPase activity can be determined in the presence of 2 mM azide and 0.1 mM vanadate, inhibitors of the F- and P-type ATPases. Oligomycin and ouabain, inhibitors of the F-type (mitochondrial ATPase) and $Na^+/K^+$ ATPase can also be included. ATP hydrolysis is monitored spectrophotometrically, by following the depletion of NADH in an enzyme-ATP regeneration system (Roberts et al. Methods of Enzymol. 194:644–661), or alternatively by determination of inorganic phosphate (Bowman et al., 1988 Proc. Natl. Acad. Sci. USA 85:7972–7976; Boyd et al., 2001, J. Pharmacology and Experimental Therapeutics 297:114–120).

In addition, membrane vesicles enriched with V-ATPase activity accumulate proton in an ATP dependent manner. The assay is done in the presence of fluorescent weak bases that accumulate in the acidifying organelles and consequently undergo changes in their adsorption or fluorescent spectra. Alternatively, cells are allowed to internalize pH-sensitive fluorochrome coupled to dextran, endosomes are isolated, and ATP dependent change in pH can then be monitored. Such assays have been employed to determine V-ATPase mediated proton translocations in membrane vesicles derived from various acidic compartments such as chromaffin granules (Nelson, Cdon et al. 1988), endocytic vesicles and lysosomes (Gallaway, Dean et al. 1988), Golgi membranes (Gallaway, Dean et al. 1988; Yeh and Rossum 1991) coated vesicles stripped of clathrin (Arai, Berne et al. 1987) and in liposomes containing reconstituted V-ATPase (Arai, Berne et al. 1987; Wang and Gluck 1990). Several weak bases have been employed: i.e. acridine orange (Arai, Berne et al. 1987) quinacrine (Bowman, Siebers et al. 1988) and amino-6-chloro-2-methoxy-acridine (Xu and Forgac 2001).

In non-limiting embodiments of the invention, a reaction mixture of V-$H^+$-ATPase, a test compound and substrate is prepared and the activity of V-$H^+$-ATPase is compared to the activity observed in the absence of the test compound wherein decrease in the level of V-$H^+$-ATPase activity in the presence of the test compound indicates that a V-$H^+$-ATPase antagonist has been identified. Alternatively, a reaction mixture of V-$H^+$-ATPase, a test compound and substrate is prepared and the activity of V-$H^+$-ATPase is compared to the activity observed in the absence of the test compound wherein an increase in the level of V-$H^+$-ATPase enzyme activity in the presence of the test compound indicates that a V-$H^+$-ATPase agonist has been identified.

5.2.2. Cell Based Screening Assays for Compounds Useful in Modulating the Activity of V-$H^+$-ATPASE and AVO Function/Acidification In accordance with the invention, a cell based assay system can be used to screen for compounds that modulate the function and/or acidification of AVO. In a specific embodiment of the invention, a cell-based assay system can be used to screen for compounds that modulate the activity of V-$H^+$-ATPase and thereby, modulate the function of AVO and/or acidification of AVO within a cell, thereby modulating cellular sensitivity to radiation or chemotherapeutic exposure. To this end, cells that express V-$H^+$-ATPase can be used to screen for compounds.

The present invention provides methods for identifying compounds that alter the enzymatic activity of V-$H^+$-ATPase, i.e., hydolysis of ATP and/or ATP dependent proton translocation. Specifically, compounds may be identified that promote V-$H^+$-ATPase enzyme activities, i.e., agonists, or compounds that inhibit V-$H^+$-ATPase activities, i.e., antagonists. Compounds that inhibit V-$H^+$-ATPase activity will be inhibitory for AVO function and/or acidification. Compounds that activate V-$H^+$-ATPase activity will enhance AVO acidification. Such compounds may be compounds that interact with the active site of V-$H^+$-ATPase thereby modulating enzyme activity. Compounds that modulate ATPase activity may be those that compete with or facilitate substrate binding to V-$H^+$-ATPase. Additionally, such compounds may be those that either increase or inhibit catalysis of substrate. Alternatively, compounds may be identified that modulate the activity of proteins that modify the V-$H^+$-ATPase protein, i.e., phosphorylate, ribosylate, etc., and thereby regulate the activity of V-$H^+$-ATPase. In addition, compounds may be identified that regulate V-$H^+$-ATPase expression and thereby regulate the level of enzyme activity within a cell. Compounds may also be identified that regulate the biosynthesis of AVO within the cell.

The present invention provides for methods for identifying a compound that activates V-$H^+$-ATPase activity comprising (i) contacting a cell expressing V-$H^+$-ATPase with a test compound and measuring the level of V-$H^+$-ATPase activity; (ii) in a separate experiment, contacting a cell expressing V-$H^+$-ATPase with a vehicle control and measuring the level of V-$H^+$-ATPase activity where the conditions are essentially the same as in part (i), and then (iii) comparing the level of V-$H^+$-ATPase activity measured in part (i) with the level of V-$H^+$-ATPase activity in part (ii), wherein an increased level of V-$H^+$-ATPase activity in the presence of the test compound indicates that the test compound is a V-$H^+$-ATPase activator. In a further embodiment of the invention, step (i) and (ii) may be performed using a cell exposed to radiation or chemotherapy.

The present invention also provides for methods for identifying a compound that inhibits V-$H^+$-ATPase enzyme activity comprising (i) contacting a cell expressing V-$H^+$-ATPase with a test compound and measuring the level of V-$H^+$-ATPase activity; (ii) in a separate experiment, contacting a cell expressing V-$H^+$-ATPase with a vehicle control and measuring the level of V-$H^+$-ATPase activity, where the conditions are essentially the same as in part (i) and then (iii) comparing the level of V-$H^+$-ATPase activity measured in part (i) with the level of V-$H^+$-ATPase activity in part (ii), wherein a decrease level of V-$H^+$-ATPase activity in the presence of the test compound indicates that the test compound is a V-$H^+$-ATPase inhibitor. In a further embodiment of the invention, step (i) and (ii) may be performed using a cell exposed to radiation or chemotherapy.

Depending on the assays used to detect V-$H^+$-ATPase activity, the methods described above for identifying activators and inhibitors of V-$H^+$-ATPase may include the presence or absence of exposure to radiation or chemotherapeutic agents. For example, when assaying directly for V-$H^+$-ATPase activity the presence of radiation or the chemotherapeutic reagent may not be required. However, because radiation and/or chemotherapy may induce specific isoforms of the V-H$^+$-ATPase, thus, it would be advantageous to test potential inhibitors of V-H$^+$-ATPase activity in the presence and absence of radiation and/or chemotherapy. In instances where, for example, changes in AVO production are measured it will be necessary to include radiation or chemical exposure. Those skilled in the art will be able to determine operative and optimal assay conditions by employing routine experimentation.

The ability of a test molecule to modulate the activity of V-H$^+$-ATPase may be measured using standard biochemical and physiological techniques. Responses such as activation or suppression of V-H$^+$-ATPase activity, or the production of AVOs or the acidification of AVO can be measured. An inhibitor of AVO acidification may be identified by its ability, for example, to decrease acidification as measured by acridine orange staining followed by fluorescence analysis. In particular, such techniques evaluate the acidic compartments of cells as follows. In acridine orange stained cells the cytoplasm and nucleolus fluoresce bright green and dim red, while acidic compartments fluoresce bright red (Mains and May, 1988, J. Biol. Chem. 263:7887–7894; Traganos and Darzynkiewicz, Methods in Cell Biology 41:185–194, Academic Press). The intensity of the red fluorescence is proportional to the degree of acidity and/or the volume of the cellular acidic compartment. Therefore, by comparing the mean red/green fluorescence ratio within different cell populations, a change in the degree of acidity and/or the fractional volume of the cellular acidic compartment may be measured. Cells may be stained with acridine orange for 17 minutes, removed from the plate with trypsin-EDTA and collected in phenol red-free growth medium. Green (510–530 nm) and red (>650 nm) fluorescence emission from 10,000 cells illuminated with blue (488 nm) excitation light may be measured with a FACSCalibur from Becton Dickinson (San Jose, Calif.) using CellQuest software. The red to green fluorescence ratio for individual cells may be calculated using FlowJo software (TREE STAR, Inc., San Carlos, Calif.). A decrease in the red to green ratio is consistent with a decrease in AVO acidification.

In addition, intralysosomal pH may be measured to determine whether a test compound is capable of modulating V-H$^+$-ATPase activity. pH may be monitored, for example, using the DAMP method (Anderson R G et al., Proc. Natl. Acad. Sci USA, 81:4838–4842). DAMP is a weak base that accumulates in acidic compartments. The molecule is retained at the site of accumulation after aldehyde fixation and is detectable by immunogold electron microscopy because it contains a dinitrophenol group that can be detected using an anti-dinitrophenyl antibody. Accumulation of DAMP specific particles can be observed in lysosome-like multivesiclar structures of DAMP treated cells. Compounds capable of decreasing the level of detectable DAMP would be identified as antagonists.

The pattern of growth inhibition obtained by specific inhibitors of V-ATPase such as bafilomycin A1, concanamycin, and benzolactone enamides in the NCI in vitro anticancer drug discovery screen, is closely correlated (Boyd et al. 2001 J. Pharmacology and Experimental Therapeutics 297:114–120). Therefore, compounds can be tested for their effect on cell growth in the NCI screen. The results will be subjected to COMPARE analysis (Boyd and Paull, 1995 Drug Dev Res 34:91–109). A high correlation with profiles obtained by known inhibitors of V-ATPase will implicate the compound as a modulator of the enzyme. Such compounds will further be tested for their effect on acidification of intracellular organelles and on the activity of the V-ATPase in non-cell based methods.

In addition, compounds can be screened/tested by studying their effect on the acidification of intracellular organelles. Inhibitors of V-ATPase abrogate accumulation of lysosomotropic agents in acidic organelles. Weak bases such as acridine orange will be employed in these assays (Paglin et al., 2001 Cancer Research 61:439–444). Irradiated and non-irradiated MCF-7, LoVo, LNCaP cells can be used. Compounds that inhibit acidification of intracellular organelles will be further tested in non-cell based assays.

5.2.3. Assay for Compounds that Regulate the Expression of V-H$^+$-ATPase

In accordance with the invention, a cell based assay system can be used to screen for compounds that modulate the expression of V-H$^+$-ATPase within a cell. As used herein expression of V-H$^+$-ATPase refers to expression of any of the subunits comprising V-H$^+$-ATPase. In a specific embodiment of the invention, compounds may be utilized which interfere with expression of subunit c of the V-H$^+$-ATPase (Gillespie, G A et al., 1991, Proc. NAtl. Acad. Sci USA 88:4289–4293). Subunit c is an integral membrane proteolipid that is part of the V-H$^+$-ATPase proton channel and essential for the function of the ATPase. Alternatively, compounds may be used that interfere with the expression of V-H-ATPase subunit A and B2 genes (Van Hille B et al., 1993, J. Biol. Chem. 268:7050–0780; Lee B S et al., 1995, J. Biol. Chem. 270:7320–7329) as well as the expression of genes encoding proteins involved in the autophagy pathway such as Apg5 and Apg12 (Hannon E M et al., 1998, FEBS Lett. 425:391–395; Mizushima N et al., 1998, 273:33889–33892).

Assays may be designed to screen for compounds that regulate V-H$^+$-ATPase expression at either the transcriptional or translational level. In one embodiment, DNA encoding a reporter molecule can be linked to a regulatory element of the V-H$^+$-ATPase genes encoding V-H$^+$-ATPase and used in appropriate intact cells, cell extracts or lysates to identify compounds that modulate V-H$^+$-ATPase gene expression. Such reporter genes may include but are not limited to chloramphenicol acetyltransferase (CAT), luciferase, β-glucuronidase (GUS), growth hormone, or placental alkaline phosphatase (SEAP). Such constructs are introduced into cells thereby providing a recombinant cell useful for screening assays designed to identify modulators of V-H$^+$-ATPase subunit gene expression.

Following exposure of the cells to the test compound, the level of reporter gene expression may be quantitated to determine the test compound's ability to regulate V-H$^+$-ATPase expression. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemiluminescent assays such as those described in Bronstein, I. et al. (1994, *Biotechniques* 17: 172–177). Such assays provide a simple, sensitive easily automatable detection system for pharmaceutical screening.

In an embodiment of the invention, the level of V-H$^+$-ATPase expression can be modulated using antisense or ribozyme approaches to inhibit or prevent translation of V-H$^+$-ATPase mRNA transcripts or triple helix approaches to inhibit transcription of the V-H$^+$-ATPase genes. Such approaches may be utilized to treat cancers where inhibition of V-H+-ATPase expression is designed to increase the sensitivity of neoplastic cells to radiation or chemotherapeutic exposure.

Antisense approaches involve the design of oligonucleotides (either DNA or RNA) that are complementary to V-H+-ATPase mRNA. The antisense oligonucleotides will bind to the complementary mRNA transcripts and prevent translation. Absolute complementarity, although preferred, is not required. One skilled in the art can ascertain a tolerable degree of mismatch by use of standard procedures to determine the melting point of the hybridized complex.

In yet another embodiment of the invention, ribozyme molecules designed to catalytically cleave V-H+-ATPase mRNA transcripts can also be used to prevent translation of V-H+-ATPase mRNA and expression of V-H+-ATPase. (See, e.g., PCT International Publication WO90/11364, published Oct. 4, 1990; Sarver et al., 1990, Science 247:1222–1225). Alternatively, endogenous V-H+-ATPase gene expression can be reduced by targeting deoxyribonucleotide sequences complementary to the regulatory region of the V-H+-ATPase gene (i.e., the V-H+-ATPase promoters and or enhancers) to form triple helical structures that prevent transcription of the V-H+-ATPase gene within cells in the body. (See generally, Helene, C. et al., 1991, Anticancer Drug Des. 6:569–584 and Maher, L J, 1992, Bioassays 14:807–815).

The oligonucleotides of the invention, i.e., antisense, ribozyme and triple helix forming oligonucleotides, may be synthesized by standard methods known in the art, e.g., by use of an automated DNA synthesizer (such as are commercially available from Biosearch, Applied Biosystems, etc.). Alternatively, recombinant expression vectors may be constructed to direct the expression of the oligonucleotides of the invention. Such vectors can be constructed by recombinant DNA technology methods standard in the art. In a specific embodiment, vectors such as viral vectors may be designed for gene therapy applications where the goal is in vivo expression of inhibitory oligonucleotides in targeted cells.

5.2.4. Compounds that can be Screened in Accordance with the Invention

The assays described above can identify compounds which modulate V-H+-ATPase activity. For example, compounds that affect V-H+-ATPase activity include but are not limited to compounds that bind to V-H+-ATPase, and either increase enzyme activities (agonists) or inhibit enzyme activities (antagonists). Alternatively, compounds may be identified that do not bind directly to V-H+-ATPase but are capable of altering V-H+-ATPase activity by altering the activity of a protein that regulates V-H+-ATPase activity. Further, compounds that affect V-H+-ATPase subunit gene activity (by affecting V-H+-ATPase subunit gene expression, including molecules, e.g., proteins or small organic molecules, that affect transcription or interfere with splicing events so that expression of the full length or the truncated form of the V-H+-ATPase can be modulated) can be identified using the screens of the invention.

The compounds which may be screened in accordance with the invention include, but are not limited to, small organic or inorganic compounds, peptides, antibodies and fragments thereof, and other organic compounds (e.g., peptidomimetics) that bind to V-H+-ATPase and either mimic the activity triggered by any of the known or unknown substrates of V-H+-ATPase (i.e., agonists) or inhibit the activity triggered by any of the known or unknown substrates of V-H+-ATPase (i.e., antagonists). Compounds that bind to V-H+-ATPase and either enhance V-H+-ATPase activity, i.e., agonists, or compounds that inhibit V-H+-ATPase activity, i.e., antagonists, in the presence of radiation or chemotherapeutic exposure will be identified.

Specific examples of useful compounds may include, but are not limited to, peptides such as, for example, soluble peptides, including but not limited to members of random peptide libraries (see, e.g., Lam, K. S. et al., 1991, Nature 354:82–84; Houghten, R. et al., 1991, Nature 354:84–86); or combinatorial chemistry-derived molecular libraries made of D- and/or L-configuration amino acids; phosphopeptides, including, but not limited to, members of random or partially degenerate, directed phosphopeptide libraries; see, e.g., Songyang, Z. et al., 1993, Cell 72:767–778; and polyclonal, monoclonal, humanized, anti-idiotypic, chimeric or single chain antibodies, FAb, F(ab')$_2$ and FAb expression library fragments, and epitope binding fragments thereof.

Other compounds which may be screened in accordance with the invention include but are not limited to small organic molecules that affect the expression of the V-H+-ATPase subunit genes by interacting with the regulatory region or transcription factors involved in gene expression; or such compounds that affect the enzyme activities of the V-H+-ATPase or the activity of some other factor involved in modulating V-H+-ATPase activity, such as for example, a protein that phosphorylates V-H+-ATPase and thereby inactivates V-H+-ATPase activity.

5.3 Compositions Containing Modulators of V-H+-ATPase and their Uses

The present invention provides for methods of modulating V-H+-ATPase activity and/or the function/acidification of AVO. In a specific embodiment of the invention the activity of V-H+-ATPase and/or the function/acididication of AVO may be modulated using a method comprising contacting a cell with an effective amount of a V-H+-ATPase modulating compound, such as a V-H+-ATPase agonist or antagonist identified using the assays as set forth above. An "effective amount" of the V-H+-ATPase inhibitor, i.e., antagonist, is an amount that decreases the level of V-H+-ATPase activity and/or the level of AVOs expressed within a cell and/or the level of AVO acidification that is associated with a detectable decrease in V-H+-ATPase enzyme activity as measured by one of the above assays. An "effective amount" of the V-H+-ATPase activator, i.e., agonist, is an amount that subjectively increases V-H+-ATPase activity and the level of AVO expression within a cell and/or the level of AVO acidification that is associated with a detectable increase in V-H+-ATPase associated ATPase activity as measured by one of the above assays.

The present invention further provides methods of modulating the sensitivity of cells to radiation or chemotherapeutic exposure in a subject comprising administering to the subject a composition comprising a compound that modulates V-H+-ATPase activity. The composition may comprise an amount of V-H+-ATPase activator or inhibitor, or modulators of V-H+-ATPase subunit expression. Accordingly, the present invention provides for compositions comprising V-H+-ATPase activators and inhibitors.

In non-limiting embodiments, the present invention may be directed toward decreasing the survival of cells in a population of cells. Such methods may be particularly applicable to the treatment of malignant disorders of cell proliferation. In preferred embodiments of the invention, the malignant disorder to be treated may be breast cancer, colon cancer, prostate cancer, lung cancer or pancreatic cancer.

The present invention may further be directed toward promoting cell death. For example, the invention may be directed toward the disorders of cell proliferation set forth above. Disorders of epithelial cell proliferation may be particularly responsive to the methods of the invention.

The present invention provides for compositions comprising an effective amount of a compound capable of modulating V-$H^+$-ATPase activity and/or the function/acidification of AVO in a pharmaceutically acceptable carrier. Compounds include but are not limited to those capable of modulating the activity of V-$H^+$-ATPase, or the expression of V-$H^+$-ATPase and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The invention provides for improved treatment or prevention of various diseases and disorders traditionally treated by radiation therapy and/or other cytotoxic agents, by administration of a compound that regulates the expression or activity of V-$H^+$-ATPase. Such compounds include but are not limited to V-$H^+$-ATPase subunit antisense nucleic acids and V-$H^+$-ATPase agonists and antagonists. In a further non-limiting embodiment of the invention, disorders produced by the toxic side effects of radiation or chemotherapy may be prevented by administration of a compound that regulates V-$H^+$-ATPase activity. Such diseases include but are not limited to secondary malignancies and fibrosis.

In addition, compounds may be identified that stimulate, i.e., act as agonist, of V-$H^+$-ATPase. Such compounds may be utilized to prevent radiation induced damage to non-targeted cells and would preferably be administered prior to radiation or chemotherapeutic exposure.

The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing V-$H^+$-ATPase are exposed to or otherwise administered a therapeutic compound and the effect of such a therapeutic upon V-$H^+$-ATPase activity is observed. In a specific embodiment of the invention the ability of a compound to regulate, i.e., inhibit or activate V-$H^+$-ATPase activity and/or AVO function/acidification will also be tested for in vivo activity using, for example, an animal model system.

The invention provides methods of treatment and/or prophylaxis by administration to a subject of an effective amount of a compound of the invention. In a preferred aspect, the compound is substantially purified. The subject is preferably an animal, and is preferably a mammal, and most preferably human.

Various delivery systems are known and can be used to administer a compound capable of regulating V-$H^+$-ATPase activity, or V-$H^+$-ATPase subunit expression, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429–4432). Methods of introduction include but are not limited to intrader mnal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body, for example, to the region of the body targeted for radiation exposure; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In preferred embodiments of the invention, the drug is administered subcutaneously.

In addition, compositions of the invention may be conjugated to different types of reagents capable of targeting the compositions to a specific cell type. For example, the compositions may be conjugated to antibodies, ligands and receptors that have a binding affinity for the surface of targeted cells.

The present invention also provides pharmaceutical compositions. Such compositions comprise a therapeutically effective amount of a compound capable of regulating V-$H^+$-ATPase activity or V-$H^+$-ATPase subunit expression and a pharmaceutically acceptable carrier. In a specific embodiment, the term "pharmaceutically acceptable" means approved by a regulatory agency of the Federal or a state government or listed in the U.S. Pharmacopeia or other Generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The amount of the compound of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems.

In a specific, non-limiting embodiment of the invention a patient may be exposed to a concentration of at least between 1 μg/kg and 2 mg/kg bafilomycin, daily. In yet another embodiment of the invention cancer cells may be exposed to a concentration of at least between 50 μg/kg and 1.25 mg/kg, daily. In a preferred embodiment of the invention cancer cells may be exposed to a concentration of at least between 100 μg/kg and 1 mg/kg, daily. Additionally, effective doses for any particular subject in need of treatment may be determined using standard clinical techniques.

In a non-limiting embodiment of the invention, the compound, such as for example bafilomycin A1, will be administered to the subject in need of treatment prior to the initiation of radiation or chemotherapy. Alternatively, administration of the compound may commence at the same time radiation or chemotherapy initiates. Effective times for commencement of treatment and the duration of treatment will be determined experimentally using standard clinical techniques. It is understood that the course of treatment will depend on the disease state and health of the subject to be treated.

The invention also provides a pharmaceutical pack or kit comprising one or more containers filled with one or more of the ingredients of the pharmaceutical compositions of the invention, optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

Cancer Cells Respond to Radiation by Autophagy and the Increased Formation/Acidification of Acidic Vesicles

6.1 Materials and Methods 6.1.1. Cell Culture

MCF-7 (human breast adenocarcinoma), LoVo (human colon adenocarcinoma) and LNCaP (human prostate carcinoma) were obtained from the American Type Culture Collection. Cells were maintained as described in Paglin et al., 1997, Biochem. Biophs. Res. Comm. 237:678–684). Irradiation was carried out 48 hours post-plating ($T_0$) at room temperature using a Cs-137 irradiator (Sheperd Mark-I, model 68, SN643) at a dose rate of 2.43–2.32 Gy/min. Bovine aortic endothelial cells were grown and treated with $H_2O_2$ as described in Haimovitz-Friedman et al., 1994, J. Exp. Med. 180:525–535 and Verhij et al., 1996, Nature 380:75–79. Phorbol 12-myristate 13-acetate (PMA; Alexis Biochemicals Corp., San Diego, Calif.) was dissolved in dimethyl sulfoxide (DMSO) and added to cells for the duration of one hour. The final DMSO concentration was 0.03%. The cells were then rinsed with warm growth medium before being returned to the incubator for an additional 48 hours.

bFGF was added to cultures of MCF-7 cells at 10 ng/ml for 48 hours. TNF was added at 2.3 nM for 48 hours. PMA was added for 1 hour at a concentration of 30 nM, followed by rinsing of the cells and incubation for an additional 48 hours.

6.1.2. Supravital Cell Staining with Acridine Orange

Cell staining was performed according to standard techniques (Arvan et al., 1984, J. Bio. Chem. 259:13567–13572; Mains and May, 1988, J. Biol. Chem. 263:7887–7894; Traganos and Darzynkiewicz, Methods in Cell Biology 41:185–194, Academic Press). Acridine orange (Polysciences, Warrington, Pa.) was added to a final concentration of 1 μg/ml for 15 minutes. Bafilomycin A1 (Sigma Chemical Co., St. Louis, Mo.) was dissolved in DMSO and added to the cells 30 minutes prior to the addition of acridine orange. LysoSensor Blue DND-167 (Molecular Probes, Eugene, Oreg.) at a final concentration of 10 μM was added for 8 minutes. Pictures were obtained with a fluorescence microscope (Olympus BH-2 RFCA), equipped with a mercury-100 W lamp, 490 nm band pass blue excitation filters, 500 nm dichroic mirror and a 515 nm long pass barrier filter. Images of control and irradiated cells were recorded on Kodak Elite II 100 ASA film for color slides by 4 seconds exposure.

6.1.3. Determination of Mean Red/Green Fluorescence Ratio in Acridine Orange Stained Cells Using Flow Cytometry In acridine orange stained cells the cytoplasm and nucleolus fluoresce bright green and dim red, while acidic compartments fluoresce bright red (Mains and May, 1988, J. Biol. Chem. 263:7887–7894; Traganos and Darzynkiewicz, Methods in Cell Biology Vol. 41, pp. 185–194, Academic Press). The intensity of the red fluorescence is proportional to the degree of acidity and/or the volume of the cellular acidic compartment. Therefore, by comparing the mean red/green fluorescence ratio within different cell populations, a change in the degree of acidity and/or the fractional volume of the cellular acidic compartment could be measured. Cells were stained with acridine orange for 17 minutes, removed from the plate with trypsin-EDTA and collected in phenol red-free growth medium. Green (510–530 nm) and red (>650 nm) Fluoresence emission from 10,000 cells illuminated with blue (488 nm) excitation light was measured with a FACSCalibur from Becton Dickinson (San Jose, Calif.) using CellQuest software. The red to green fluorescence ratio for individual cells was calculated using FlowJo software (TREE STAR, Inc., San Carlos, Calif.). To control for possible effect of trypsinization on the measured red to green fluorescence ratio, the ratios were compared by flow cytometry with those obtained with a Laser Scanning Microscope (LSM510 from Zeiss). Stained cells, grown on cover glass, were illuminated with a 488 nm argon laser beam. The red (>650 nm) to green (505–545 nm) fluorescence ratio of an entire image was obtained using software LSM 510 version 2.01 SP2. These measurements yielded similar results to those obtained with flow cytometry. All determinations of red to green fluorescence ratio reported in this section were obtained via flow cytometry.

6.1.4. Electron Microscopy

Cell processing for electron microscopy and staining with N-(3-(2,4-dinitrophenyl)-N-(3-aminopropyl))methylamine dihydrochloride (DAMP; Molecular Probes, Eugene, Oreg.) was performed as set forth in Anderson et al., 1984, Proc. Natl. Acad. Sci. U.S.A. 81:4838–4842 and Dunn et al., 1990, J. Cell Biol. 110:1935–1945. The fraction of the cytoplasmic volume occupied by AVO (fractional volume of AVO) was quantified from electron micrographs according to Dunn and Lenk et al., (Dunn et al., 1990, J. Cell Biol. 110:1935–1945; Lenk et al., 1992, J. Cell Biol. 118:301–308). Digital Images of the micrographs were obtained using an Epson ES-1200S flat bed scanner with Adobe Photoshop version 5. The fractional volume was calculated with Image Pro Plus Version 3 and expressed as a percentage of the total cytoplasmic volume.

6.1.5. Detection of Nucelosomal Fragmentation of Genomic DNA

DNA extraction and electrophoresis on agarose gel was carried out according to Bose et al., 1995, Cell 82:405–414. DNA preparation and resolution with pulse field gel electrophoresis (PFGE) was conducted as described in Gilles et al., 2000, Blood 95:2930–2936 utilizing the CHEF Mapper (Bio-Rad, Richmond, Calif.). DNA strand breaks were assayed by the TUNEL method and analyzed by flow cytometry (Haimovitz-Friedman, 1994, J. Exp. Med. 180:525–535).

6.1.6. Gel Electrophoresis and Western Blotting

Cells were scraped and collected in PBS containing protease inhibitors (Complete and pep statin A; Boehringer Mannheim) and lysed in 2% SDS by heating at 95° C. Protein content was determined with BCA reagent (Pierce). PAGE and immunoblotting were performed (O'Farrell, 1975, J. Biol. Chem. 250:4007–4021) using anti-LAMP-1 antibodies (Hybridoma Bank, The Department of Biological Sciences, Iowa City, Iowa).

6.1.7. Immunohistochemistry

Cells were fixed with 3% formaldehyde, permeabilized with 1% triton-X-100 and stained with anti-LAMP-1 and Texas-Red conjugated anti-mouse IgG (Jackson Immunoresearch Laboratores, Inc., Jackson, Ill.).

6.1.8. Determination of Surviving Fraction

Cells were plated in growth medium at a density of 30–90 cells per square centimeter and irradiated 22 hours later. Each experimental condition was done in quintet or triplicate. Cells were irradiated at room temperature in Cs-137 Irradiator (Sheperd Mark-I, Model 68, SN 643) at a rate of 2.43–2.32 Gy/min. Six days later, 90–95% of the grown colonies possessed more than 50 cells. For determination of their red to green ratio, colonies were processed as described above. For determination of surviving fractions cells were stained with crystal violet and colonies containing 50 cells or more were counted with a dissecting microscope. The surviving fraction was defined as the ratio between the plating efficiencies of irradiated and non-irradiated cells and was calculated at each dose level according to Hall and Phill (1994, *Radiology for the Radiologist*, 4th Edition, J. Lippincott Co., Philadelphia).

6.1.9. RNA Analysis

MCF-7 (human breast adenocarcinoma), LoVo (human colon adenocarcinoma) and LNCaP (human prostate carcinoma) were grown and irradiated with 10 Gy as described before (Paglin et al., 2001, Cancer Research 61:439–444). Cells were harvested 48 hours following irradiation and total RNA was isolated with TRI Reagent® LS (MRC, Inc. Cincinnati Ohio) by following the manufacturer's protocol. Northern analysis of mRNA level was performed according to published procedures (Ausubel F. M. et al., eds., 1989, Current Protocols in Molecular Biology, Vol. I, Green Publishing Associates, Inc., and John Wiley & sons, Inc., New York). Clones for lysosomal associated membrane protein-1 (LAMP-1) and for subunit c of the V-H$^+$-ATPase were obtained from IncyteGenomics (ID # 3355576 and 243234 respectively), and cDNA probes were prepared (Davis et al. 1994, Basic Methods in Molecular Biology. Norwalk, Conn., Appleton & Lange) and labeled with $^{32}$P with Prime-It® II Random Priming Labeling kit from Stratagene.

6.2 Results and Discussion

The experiments set forth herein indicated that human breast cancer cells are sensitive to standard doses of radiation. Following radiation with 6 Gy, ~5% of the cells remained clonogenic. Nonetheless, the cells did not show any of the biochemical and morphological changes that are associated with apoptosis up to four days following irradiation with 10 Gy. At four days following irradiation, 30 percent of the cells were already dead and did not exclude trypan blue. Still, nucleosomal ladder formation and a positive TUNEL reaction could not be demonstrated (FIG. 1). Furthermore, electron microscopy did not reveal the morphological changes that are typical of apoptosis, namely chromatin margination and condensation (FIG. 2). Instead, DNA damage was manifested by micronuclei formation (Paglin et al., 1997, BBRC 237:678–687) and non-discrete DNA degradation (FIG. 1).

An evaluation for Type II programmed cell death-related cellular events, such as changes in cellular acidic compartments was performed. For detecting the acidic compartment, the lysosomotropic agent acridine orange was used. It is a weak base that moves freely across biological membranes when uncharged. Its protonated form accumulates in acidic compartments where it forms aggregates that fluoresce bright red (Arvan et al., 1984, J. Bio. Chem. 259:13567–13572; Mains and May, 1988, J. Biol. Chem. 263:7887–7894; Traganos and Darzynkiewicz, Methods in Cell Biology Vol. 41, pp. 185–194, Academic Press). Vital staining of MCF-7 cells with acridine orange revealed the appearance of acidic vesicular organelles (AVO) following irradiation. Concentrated dye in the vesicles fluoresced bright red while the cytoplasm and the nucleus showed dominant green fluorescence (FIG. 3A(b)). In contrast, the majority of unirradiated cells exhibited mainly green fluorescence with minimal red fluorescence (FIG. 3A(a)). In numerous studies, demonstration of vacuolar proton ATPase (V-H$^+$-ATPase)-dependent acidification of cellular organelles, as well as its involvement in different cellular processes, was achieved by employing its specific inhibitor bafilomycin A1 (Bowman et al., 1988, Proc. Natl. Acad. Sci. U.S.A. 85:7972–7976; Gagliardi et al., 1999, Current Medicinal Chem. 6:1197–1212). Similarly, by addition of the inhibitor to MCF-7 cells it was demonstrated that acidification of AVO is mediated by the V-H$^+$-ATPase (FIG. 3A (c,d)). Pre-incubation of the cells with 300 $\mu$M of the weak amine chloroquine also inhibited acridine orange accumulation in the AVO.

To measure the radiation-induced increase in fractional volume and/or acidity of AVO, the mean red to green fluorescence ratio in control and irradiated cells was determined. At 24 hours following sham irradiation, 92% of the unirradiated controls were tightly distributed around their mean red/green fluorescence ratio (FIG. 3B(a)). Only 8% had a red/green fluorescence ratio that increased asymptotically above 2 (the highest value in the descending limb of the histogram). On the other hand, 55% of the irradiated cells had red/green ratio that was higher then 2, and the mean value of red/green fluorescence ratio was 2.3 fold higher than in controls (FIG. 3B(b)). Bafilomycin A1 decreased the mean red/green fluorescence ratio in unirradiated cells and also inhibited its radiation-induced increase. In the presence of bafilomycin A1, the mean red/green fluorescence ratio was similar in both unirradiated and irradiated cells, indicating that the radiation-induced increase in this ratio is due to development of AVO, rather than other possible changes in the molecular composition of the irradiated cells (FIG. 3B(c,d)). AVO appearance was dependent upon radiation dose and increased with time following irradiation (FIG. 4).

To further differentiate between the acidic compartments of control and irradiated cells, an additional lysosomotropic agent—LysoSensor Blue DND-167 was used. The fluorescence of LysoSensor Blue is pH-dependent and increases as pH decreases. In unirradiated cells, LysoSensor Blue hardly showed any fluorescence while irradiated cells fluoresced bright blue (FIG. 3A(e,f)), indicating that the pH of the acidic compartments in irradiated cells is indeed lower than that of unirradiated cells. AVO appearance was associated with increased levels of the lysosomal membrane protein LAMP-1 as evident from western blot analysis and immunocytochemistry (FIGS. 5A,B).

The increase in red to green fluorescence ratio could be modulated by phorbol 12 myristate 13-acetate (PMA). The mean red to green fluorescence ratio increased by a factor of 1.7±0.3 (n=3) 48 hours following stimulation with 30 nM PMA. This result suggests that protein kinase C may be involved in the increased red to green fluorescence ratio following irradiation.

The increase in the mean red to green fluorescence ratio following irradiation was also observed in two other cancer cell lines. Forty-eight hours following irradiation with 10 Gy, the mean red/green fluorescence ratio increased in prostate cancer (LNCaP) and in colon adenocarcinoma (LoVo) cells by 1.6±0.1 (n=3) and 2±0.2 (n=3) fold respectively. As in MCF-7 cells, the increase in the mean red to green fluorescence ratio in LoVo and LNCaP cells was associated with the appearance of red fluorescent vesicular organelles.

Parallel investigations with electron microscopy confirmed the radiation-induced formation of a new acidic compartment (FIGS. 2A,B). These subcellular organelles were composed of core vesicles with granular, vesicular or lamellar content. The core vesicles were often surrounded by and intertwined with smooth or part smooth/part rough membrane cisternae that were found to fuse with smooth vesicles of unknown origin (FIG. 2B). The diameter of these organelles ranged from 0.5–2.5 $\mu$M and was comparable to the diameter of the largest red fluorescent AVO in irradiated cells. Because fluorescent AVO may consist of an heterogeneous population of acidic organelles, we termed the ones characterized by electron microscopy—AVO-EM. AVO-EM were found to be acidic by virtue of their ability to concentrate the lysosomotropic agent, (N-(3-(2,4dinitrophenyl)-N-(3-aminopropyl)methylamine, dihydrochloride (DAMP) (FIG. 2C). By 48 hours post-irradiation with 10 Gy the average fractional volume of AVO-EM in the population was 16±0.1% (FIG. 2D), while in unirradiated cells their average fractional volume was 0.91±0.01%. The emergence of AVO-EM during the first 48 hours post irradiation with 2–10 Gy was dose- and time-dependent.

During autophagy, portions of the cytoplasm and subcellular organelles are sequestered by the endoplasmic reticulum, resulting in vesicular bodies that are bound by double membrane cisternae (Bloommaart, E F C et al., 1997, Biochemical Journal 29:365–385). The association of the core vesicles with membrane cisternae in AVO-EM bears morphological similarities to autophagous bodies. The effect of 3-methyladenine, an inhibitor of autophagy (Bloommaart, E F C et al., 1997, Biochemical Journal 29:365–385; Seglan P O et al., 1982, Proc Natl Acad Sci USA 79:1889–1892), on AVO formation was examined. 3-methyladenine at final concentration of 5 mM decreased the red to green ratio at 48 hours following radiation with 10 Gy from 1.77±0.01 to 1.15±0.01 (n=3). Electron microscopy analysis demonstrated a parallel reduction in the fraction of cells containing AVO-EM from 94% to 22%. The effect of 3-methyladenine on irradiated cells suggests that the formation of AVO after irradiation may share similar pathways with processes that regulate autophagy.

It is noteworthy that in addition to ionizing irradiation, other death-inducing agents such as TNF and staurosporin kill MCF-7 without producing typical apoptotic changes (Janicke R et al., 1998, J. Biol. Chem. 273:9357–9360). It has recently been reported that the lack of apoptotic response to TNF results from absence of caspase-3 in these cells (Janicke R et al., 1998, J. Biol. Chem. 273:9357–9360). The absence of caspase-3 may well explain the lack of apoptotic response to ionizing irradiation. z-VAD-fmk (Enzyme Systems Products, Livermore, Calif.) was added to cells 1 hour before irradiation. Cells were harvested 24 hours following irradiation and processed for determination of their mean red to green fluorescence ratio. The emergence of AVO in the presence of the pan-caspase inhibitor z-VAD-fmk at concentrations ranging from 50–154 $\mu$M (Table 1) suggests that the programmed events that lead to AVO formation are not related to apoptosis.

TABLE 1

| Caspases do not mediate AVO formation | | |
|---|---|---|
| z-VAD-fmk (50 $\mu$M) | − | + |
| unirradiated | 1.2 ± 0.05 | 1.4 ± 0.07 |
| 10 Gy | 2.3 ± 0.08 | 2.5 ± 0.04 |

Numbers are means ± S.D from triplicates samples of one experiment that was reproduced twice at 50 $\mu$M and 154 $\mu$M Cells that survive radiation may continue to divide and form colonies, even though their DNA might have sustained damage (Revell, S et al., 1983, Relationship Between Chromosome Damage and Cell Death 4:215–233. New York: Alan R. Liss). Bafilomycin A1 was added to irradiated cells at the time of irradiation for 24 hours. Red to green ratio in colonies was determined as described above. The numbers are mean±S.D from three separate experiments.

As demonstrated in Table 2 progenies of irradiated cells contain an increased level of AVO suggesting that the emergence of acidic compartments protects the cells against radiation damage. The effect of bafilomycin A2 on the survival of irradiated cells was significant (P<0.05; student t test).

TABLE 2

| AVO accumulation in progenies of irradiated cells is necessary for their survival | | | |
|---|---|---|---|
| Radiation dose (Gy) | Fold increase of mean R/G | Surviving fraction | Surviving fraction in the presence of Baf A1 (2nM) |
| 0 | 1 | 1 ± 0.04 | 0.9 ± 0.14 |
| 2 | 1.2 ± 0.01 | 0.7 ± 0.09 | 0.51 ± 0.07 |
| 3 | 1.3 ± 0.1 | 0.42 ± 0.06 | 0.23 ± 0.05 |

The numbers are mean±S.D from one experiment. The surviving fraction for 0 and 2 Gy are from Table 5 and for 3 Gy from Table 8.

Experiments with bafilomycin A1 showed that inhibition of V-H$^+$-ATPase, the enzyme that mediates AVO acidification, augmented DNA degradation and decreased survival following irradiation (FIG. 6 and Table 2). Addition of bafilomycin A1 two days following iradiation with 10 Gy, for a period of 24 hours, dramatically increased DNA clevage into large fragments (20–1000 kb). Also, addition of bafilomycin A1 for 24 hours following irradiation with 2 and 3 Gy reduced the surviving fraction by 30%–40% without significantly affecting the survival of unirradiated cells.

The effect of 8 nM bafilomycin A1 on the clonogenic survival of irradiated cells is presented in Table 3. Cells were plated and irradiated as set forth above. The surviving fractions obtained from the data was used for plotting the survival curve in FIG. 8.

TABLE 3

| Bafilomycin A1 8 nM | Radiation Gy | Plating Efficiency | Surviving Fraction | Normalized Surviving Fraction |
|---|---|---|---|---|
| − | − | 166 ± 16.5 | 1 | |
| − | 2 | 107 ± 14 | 0.66 | |
| − | 4 | 82 ± 13.5 | 0.25 | |
| − | 6 | 24 ± 6 | 0.04 | |
| + | − | 98 ± 12 | 0.59 | 1 |
| + | 2 | 43 ± 7.7 | 0.26 | 0.47 |
| + | 4 | 21 ± 3.4 | 0.06 | 0.11 |
| + | 6 | 7 ± 3 | 0.01 | 0.23 |

Table 4 and 5 demonstrate the effect of 2 nM bafilomycin A1 on survival of MCF-7 cells with increasing doses of irradiation.

TABLE 4

| Radiation Dose Gy | Surviving Fraction |
|---|---|
| 0 | 1 ± 0.05 |
| 2 | 0.70 ± 0.1 |
| 4 | 0.27 ± 0.03 |
| 6 | 0.04 ± 0.01 |
| 2 nM bafilomycin A1 | |
| 0 | 0.93 ± 0.14 |
| 2 | 0.51 ± 0.07 |
| 4 | 0.17 ± 0.02 |
| 6 | 0.02 ± 0.003 |

As demonstrated, 2 nM bafilomycin A1 alone did not have a significant effect on the survival of the cells to radiation. However, survival following irradiation with 200 cGy was decreased by 27% and by 37% following irradiation with 400 cGy.

TABLE 5

| Radiation Dose (cGy) | Surviving Fraction |
|---|---|
| 0 | 1 ± 0.06 |
| 2 | 0.70 ± 0.03 |
| 4 | 0.31 ± 0.01 |
| 6 | 0.07 ± 0.02 |
| 2 nM bafilomycin A1 | |
| 0 | 1 ± 0.07 |
| 2 | 0.57 ± 0.04 |
| 4 | 0.27 ± 0.01 |
| 6 | 0.05 ± 0.01 |

As indicated in Table 5, Bafilomycin A1 decreased cell survival following irradiation with 200 cGy by 19% and by 13% following 400 cGy of radiation.

The effect of increasing concentrations of bafilomycin A1 on the survival of MCF-7 cells following exposure to 3 Gy of radiation is depicted in Tables 6 and 7.

TABLE 6

| Treatment (nM bafilomycin) | Surviving Fraction |
|---|---|
| 0-C | 1.00 ± 0.06 |
| 0-X | 0.44 ± 0.05 |
| 2-C | 0.89 ± 0.06 |
| 2-X | 0.28 ± 0.03 |
| 4-C | 0.7 ± 0.03 |
| 4-X | 0.2 ± 0.03 |
| 8-C | 0.66 ± 0.05 |
| 8-X | 0.14 ± 0.02 |
| 16-C | 0.52 ± 0.05 |
| 16-X | 0.12 ± 0.03 |

As indicated in Table 6, 2 nM bafilomycin did not significantly affect the survival of MCF-7 cells. However at 3 Gy, 2 nM bafilomycin reduced survival by 37% (C=non-irradiated control, X=radiated).

TABLE 7

| Treatment (nM bafilomycin Al) | Surviving Fraction |
|---|---|
| 0-C | 1.00 ± 0.07 |
| 0-X | 0.43 ± 0.07 |
| 2-C | 0.92 ± 0.06 |
| 2-X | 0.22 ± 0.04 |
| 4-C | 0.79 ± 0.04 |
| 4-X | 0.16 ± 0.04 |
| 8-C | 0.60 ± 0.08 |
| 8-X | 0.12 ± 0.02 |
| 16-C | 0.35 ± 0.05 |
| 16-X | 0.09 ± 0.04 |

2 nM bafilomycin does not significantly affect the survival of MCF-7 cells. However, 300 cGy, 2 nM bafilomycin reduced cell survival by 49%.

The effect of concanamycin on the survival of MCF-7 cells exposed to radiation was tested and the results are depicted in Tables 8 and 9.

TABLE 8

| Concanamycin A (pM) | Surviving Fraction 0 Gy | Surviving Fraction 3 Gy |
|---|---|---|
| 0 | 1 ± 0.07 | 0.32 ± 0.03 |
| 1 | 1.04 ± 0.06 | 0.28 ± 0.04 |
| 3 | 0.90 ± 0.07 | 0.22 ± 0.05 |
| 10 | 0.56 ± 0.08 | 0.06 ± 0.01 |

As indicated, 3 pM concanamycin did not significantly affect the survival of MCF-7 cells, but descreased thier survival by 31% following irradiation.

TABLE 9

| Concanamycin A (pM) | Surviving Fraction 0 Gy | Surviving Fraction 3 Gy |
|---|---|---|
| 0 | 1 ± 0.07 | 0.45 ± 0.09 |
| 2 | 0.99± 0.11 | 0.28 ± 0.04 |
| 4 | 0.85 ± 0.15 | 0.18 ± 0.03 |
| 6 | 0.85 ± 0.15 | 0.14 ± 0.04 |
| 8 | 0.69 ± 0.16 | 0.10 ± 0.04 |

As indicated in Table 9, at 2 nM concanamycin did not significantly affect the survival of MCF-7 cells, but increased their radiosensitivity by 38%.

In addition, the effect of salicylihalamide A on clonogenic survival of irradiated and non-irradiated cells was determined and the results are depicted in Table 10.

TABLE 10

| Salicylihalamide A (nM) | Surviving Fraction 0 Gy | Surviving Fraction 3 Gy |
| --- | --- | --- |
| 0 | 1 ± 0.05 | 0.46 ± 0.09 |
| 12.5 | 1.14 ± 0.07 | 0.38 ± 0.03 |
| 25 | 0.92 ± 0.08 | 0.32 ± 0.03 |
| 50 | 0.72 ± 0.09 | 0.22 ± 0.04 |
| 100 | 0.53 ± 0.03 | 0.11 ± 0.02 |

As indicated in Table 10, 25 nM salicylihalamide A did not significantly affect survival of MCF-7 but descreased survival of irradiated cells by 30%.

In addition, experiments similar to those conducted using MCF-7 cells were carried out using LoVo cells. The effect of increasing concentrations of bafilomycin A1 on clongenic survival of irradiated LoVo cells (3 Gy) is presented in Tables 11 and 12. As indicated, 2 nM bafilomycin decreased survival by 43% (Table 11) and 24% (Table 12.)

TABLE 11

| Bafilomycin A1 (nM) | Surviving Fraction 0 Gy | Surviving Fraction 3 Gy |
| --- | --- | --- |
| 0 | 1 ± 0.10 | 0.42 ± 0.06 |
| 2 | 1.14 ± 0.09 | 0.24 ± 0.08 |
| 4 | 1.01 ± 0.03 | 0.23 ± 0.02 |
| 8 | 0.84 ± 0.12 | 0.19 ± 0.04 |

TABLE 12

| Bafilomycin (nM) | Surviving Fraction 0 Gy | Surviving Fraction 3 Gy |
| --- | --- | --- |
| 0 | 1 ± 0.07 | 0.21 ± 0.02 |
| 2 | 0.92 ± 0.05 | 0.16 ± 0.01 |
| 4 | 0.84 ± 0.03 | 0.08 ± 0.02 |

The effect of 2 nm bafilomycin A1 on the resistance of LoVo cells to radiation with 2 and 3 Gy is presented in Table 13. Bafilomycin A1 decreased survival at 2 Gy by 25% and at 3 Gy by 30%.

TABLE 13

| Dose Gy | Surviving Fraction 0 Gy | Surviving Fraction 2 nM Bafilomycin |
| --- | --- | --- |
| 0 | 1 ± 0.12 | 0.78 ± 0.05 |
| 2 | 0.32 ± 0.05 | 0.24 ± 0.03 |
| 3 | 0.16 ± 0.02 | 0.11 ± 0.03 |

Increased autophagy, the hallmark of programmed cell death type II, is thought to lead to cell death via destruction of the cytoplasm. Still, the lysosomal compartment has been linked to cellular defense mechanisms such as protection against infectious agents (Steinman, R et al., 1994, J Exp Med. 179:1–30). Recently, acidic compartments have been associate with drug resistance of breast cancer cell lines (Altan, N et al., 1998, J Exp Med 187:1583–1598), and in yeast autophagy is required for cell survival during stravation (Mizushima N et al., 1998, Nature 395:395–398).

Similarly, our results suggest that accumulation of acidic organelles following irradiation is modulated by cellular defense mechanisms. These organelles may protect the cells by preventing cytoplasmic acidification, by providing catabolites required for repair processes, and/or by containing toxic molecules. The experimental data indicates that moderate formation of AVO in surviving colonies provide long-term protection against low radiation damage. However, continuous accretion of AVO following high level of damage may offset their protective effect, leading to replacement of the normal cytoplasm and possibly to necrosis and cell death. Therefore, inhibition of AVO formation or function can serve as a tool to increase cell death following low radiation damage and facilitate cell kill following high radiation damage. Modulation of AVO function may prove useful for increasing the therapeutic ratio of radiation treatment of epithelial cancers.

Subunit c of the V-H$^+$-ATPase and LAMP-1 are two components of the lysosomal system. Subunit c participates in forming the H+ channel of the enzyme (Forgac, 1999 J. Biol. Chem 274:12951–12954), while LAMP-1 is a component of the lysosomal membranes (Metzelaar and Clevers, 1992 Thromb Haemost 68:378–382). As indicated in FIG. 9, the level of mRNA for subunit c of V-H$^+$-ATPase increases in irradiated cells relative to control unirradiated cells. Although the level of LAMP-1 mRNA remained unchanged, the level of LAMP-1 protein increased following radiation (Paglin et al., 2001 Cancer Research 61:439–444) indicating that the regulation of its cellular level following irradiation is post-transcriptional. The results depicted in FIG. 9 are a representative experiment that was reproduced three times for MCF-7 and once for LoVo and LNCaP cells.

A number of experiments were conducted to determine whether inhibition of V-ATPase increased the sensitivity of cancer cells to chemotherapeutic agents, such as adriamycin and etoposide. As demonstrated in Tables 14–19 salicilyhalamide A and bifilomycin A1 descreased the survival of cells exposed to the chemotherapeutic agents adriamycin and etoposide.

The effect of 2 nM bafilomycin A1 on the resistance of cells to treatment with increasing concentration of adriamycin was tested and as demonstrated in Table 14, 2 nM bafilomycin decreased by 22% the survival of LoVo cells exposed to 100 nM Adriamycin.

TABLE 14

| Adriamycin (nM) | Surviving Fraction Without Bafilomycin | Surviving Fraction 2 nM Bafilomycin |
| --- | --- | --- |
| 0 | 1 ± 0.01 | 0.93 ± 0.05 |
| 50 | 0.84 ± 0.01 | 0.73 ± 0.08 |
| 100 | 0.77 ± 0.01 | 0.60 ± 0.05 |
| 150 | 0.47 ± 0.02 | 0.38 ± 0.03 |

The effect of bafilomycin A1 on the resistance of MCF-7 cells to 100 nM adriamycin was tested and as shown in Table 15, 2 nM bafilomycin decreased survival by 34%.

TABLE 15

| Bafilomycin (nM) | | Adriamycin |
| --- | --- | --- |
| 0 | 1 ± 0.1 | 0.88 ± 0.08 |
| 2 | 0.95 ± 0.1 | (0.56; 0.58)0.57* |
| 4 | 0.61 ± 0.05 | 0.35 ± 0.05 |

*Average of two plates.

The effect of salicilyhalamide A on survival of MCF-7 cells exposed to 100 nM adriamycin was tested and the results are shown in Table 16.

TABLE 16

| Salicilyhalamide (nM) | Surviving Fraction | Surviving Fraction 100 nM Adriamycin |
|---|---|---|
| 0 | 1 | 0.88 ± 0.08 |
| 25 | 1.03 ± 0.03 | 0.79 ± 0.05 |
| 50 | 0.95 ± 0.01 | 0.66 ± 0.04 |
| 100 | 0.78 ± 0.04 | 0.57 ± 0.01 |

As indicated in Table 16, 50 nM, salicylihalamide A alone shows minimal effect on cell survival, but decreased survival by 25% when added in combination with 100 nM Adriamycin.

Next, the effect of bafilomycin on LoVo cell resistance to Adriamycin was tested. The cells were incubated with the drugs for 48 hours.

TABLE 17

| Bafilomycin A1 (nM) | | Adriamycin 100 nM |
|---|---|---|
| 0 | 1 ± 0.15 | 0.94 ± 0.1 |
| 2 | 0.86 ± 0.04 | 0.65 ± 0.05 |
| 4 | 0.61 ± 0.04 | 0.4 ± 0.01 |

As presented in Table 17, at 2 nM, bafilomycin decreased resistance to Adriamycin by 35%.

Table 18 and Table 19, present data showing the effect of bafilomycin on cell survival in the presence of etoposide. Table 18 shows that MCF-7 survival was decreased by 54%, while Table 21 shows that LoVo survival was decreased by 25%

TABLE 18

| Etoposide (μg/ml) | | Bafilomycin A1 (2 nM) |
|---|---|---|
| 0 | 1 ± 0.08 | 0.9 ± 0.09 |
| 0.05 | (0.79; 0.77) 0.78* | 0.36 ± 0.08 |

TABLE 19

| Etoposide (μg/ml) | | Bafilomycin (2 nM) |
|---|---|---|
| 0 | 1 ± 0.01 | 1.16 ± 0.07 |
| 0.05 | 0.78 ± 0.05 | 0.59 ± 0.08 |

A variety of different cytokines and known modulators of enzymatic activities in cells were tested to determine whether such compounds were capable of affecting the content of acidic organelles in the cell. As demonstrated below, bFGF, TNF, PMA, rapamycin and tamoxifen were all capable of inducing formation of acidic organelles. The results indicate that several biochemical pathways may be targeted to modulate the formation and activity of acidic organelles following exposure to radiation or chemotherapy bFGF was added to cultures of MCF-7 cells at 10 ng/ml for 48 hours. TNF was added at 2.3 nM for 48 hours. PMA was added for 1 hour at a conc. of 30 nM, followed by rinsing of the cells and incubation for an additional 48 hours. All measurements were done 48 hours following initiation of treatment.

TABLE 20

| Effector | Fold Increase in Red: Green |
|---|---|
| bFGF | 2.23 ± 0.18 (n = 3) |
| TNF- | 2.7 ± 0.07 (n = 3) |
| PMA | 1.7 ± 0.3 (n = 3) |

Mammalian target of rapamycin (mTOR) is a negative regulator of autophagy (Bloomaart et al. 1995; J Biol. Chem 270:2320–2326; Noda and Ohsumi, 1998 J Biol Chem 273:3963–3966) and is inhibited in vivo and in vitro by rapamycin (Gingras et al., 2001 et al., Genes and Development 15:807–826) The effect of rapamycin on the formation of acidic organelles in MCF-7 cells was tested and the results suggest that inhibition of mTOR in MCF-7 cells leads to formation of acidic organelles.

TABLE 21

| Treatment | Fold Increase in Red:Green 48 hrs |
|---|---|
| 20 nM rapamycin | 1.96 |
| 50 nM rapamycin | 2.31 |
| 10 Gy | 1.70 |

TABLE 22

| Treatment | Fold Increase in Red:Green | |
|---|---|---|
| Rapamycin | 24 hrs | 48 hrs |
| 10 nM | 1.7 | 1.6 |
| 20 nM | 1.7 | 1.4 |

Tamoxifen is an anti-estrogen drug used in hormonal anti-estrogen treatment of breast cancer. The following experiment shows that tamoxifen induced formation of acidic organelles. Furthermore, addition of estrogen inhibited the effect of tamoxifen. As shown in Table 23, tamoxifen induced the appearance of acidic vesicular organelles and -estradiol inhibited by 50% the effect of tamoxifen.

TABLE 23

| Tamoxifen (M) | Estradiol (M) | Fold increase of Red:Green |
|---|---|---|
| $10^{-6}$ | | 1.5 |
| $2 \times 10^{-6}$ | | 1.6 |
| | $10^{-9}$ | 1 |
| $10^{-6}$ | $10^{-9}$ | 1.25 |
| $2 \times 10^{-6}$ | $10^{-9}$ | 1.33 |

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

We claim:

1. A method for promoting cell death of a cell which has been exposed to a chemotherapeutic agent comprising contacting said cell with benzolaetone enamide that is an inhibitor of vacuolar proton ATPase activity within about 48 hours of the first exposure to the chemotherapeutic agent in an amount effective to prevent formation of acidic vesicular organelles in said cell, thereby promoting cell death.

2. A method of promoting cell death of a cell which has been exposed to irradiation comprising contacting said cell with a plecomacrolide or a benzolaetone enamide that is an inhibitor of vacuolar proton ATPase activity in an amount effective to inhibit vacuolar proton ATPase activity in said cell, thereby promoting cell death.

3. The method of claim 1 wherein the benzolaetone enamide is a lobatamide.

4. The method of claim 1 wherein the benzolaetone enamide-is salicylihalamide A.

5. The method of claim 1 wherein the benzolaetone enamide is an oximidine.

6. A method for promoting cell death of a cell which has been exposed to a chemotherapeutic agent comprising contacting said cell with a benzolaetone enamide that is an inhibitor of acidic vesicular function or acidification within about 48 hours of the first exposure to the chemotherapeutic agent in an amount effective to prevent formation of acidic vesicular organelles in said cell, thereby promoting cell death.

7. A method of promoting cell death of a cell which has been exposed to irradiation comprising contacting said cell with a plecomacrolide or a benzolaetone enamide that is an inhibitor of acidic vesicular function or acidification in an amount effective to inhibit acidic vesicular function or acidification in said cell, thereby promoting cell death.

8. The method of claim 6 wherein the benzolactone enamide is a lobatamide.

9. The method of claim 6 wherein the benzolaetone enamide is salicylihalamide A.

10. The method of claim 2 wherein the plecomacrolide is a bafilomycin.

11. The method of claim 10 wherein the bafilomycin is bafilomycin A1.

12. The method of claim 2 wherein the plecomacrolide is a concanamycin.

13. The method of claim 2 wherein the benzolaetone enamide is a lobatamide.

14. The method of claim 2 wherein the benzolaetone enamide is salicylihalamide A.

15. The method of claim 2 wherein the benzolaetone enamide is an oximidine.

16. The method of claim 6 wherein the benzolaetone enamide is an oximidine.

17. The method of claim 7 wherein the plecomacrolide is a bafilomycin.

18. The method of claim 17 wherein the bafilomycin is bafilomycin A1.

19. The method of claim 7 wherein the plecomacrolide is a concanamycin.

20. The method of claim 7 wherein the benzolaetone enamide is a lobatamide.

21. The method of claim 7 wherein the benzolaetone enamide is an oximidine.

22. The method of claim 7 wherein the benzolaetone enamide is salicylihalamide A.

* * * * *